(12) United States Patent
Peper et al.

(10) Patent No.: US 7,208,121 B2
(45) Date of Patent: *Apr. 24, 2007

(54) PLASTICIZER-FREE-ION-DETECTIVE SENSORS

(75) Inventors: Shane Peper, Los Alamos, NM (US); Yu Qin, Auburn, AL (US); Eric Bakker, Auburn, AL (US)

(73) Assignee: Auburn University, Auburn, AL (US)

( * ) Notice: Subject to any disclaimer, the term of this patent is extended or adjusted under 35 U.S.C. 154(b) by 398 days.

This patent is subject to a terminal disclaimer.

(21) Appl. No.: 10/313,090

(22) Filed: Dec. 5, 2002

(65) Prior Publication Data

US 2003/0217920 A1    Nov. 27, 2003

Related U.S. Application Data

(60) Provisional application No. 60/337,101, filed on Dec. 6, 2001, provisional application No. 60/337,099, filed on Dec. 6, 2001.

(51) Int. Cl.
G01N 27/333   (2006.01)
G01N 21/01    (2006.01)
G01N 21/64    (2006.01)
G01N 33/20    (2006.01)

(52) U.S. Cl. .................. 422/82.03; 204/416; 204/418; 205/781.5; 422/56; 422/82.01; 422/82.02; 422/82.05; 422/82.06; 422/82.07; 422/82.08; 422/82.09; 422/82.11; 436/73; 436/74; 436/79; 436/80; 436/81; 436/82; 436/83; 436/84; 436/166; 436/169; 436/172

(58) Field of Classification Search ............ 422/55–58, 422/82.05–82.09, 82.11, 82.01–82.03; 436/73–74, 436/76–84, 164, 166, 169, 172, 52, 528, 436/531; 427/222; 204/416, 418; 205/781.5
See application file for complete search history.

(56) References Cited

U.S. PATENT DOCUMENTS 4,162,282 A    7/1979   Fulwyler et al.
(Continued)

FOREIGN PATENT DOCUMENTS

EP    0 432 990 A2    6/1991
(Continued)

OTHER PUBLICATIONS

Xie, Z. et al, Journal of the American Chemical Society 1994, 116, 1907-1913.*
(Continued)

*Primary Examiner*—Arlen Soderquist
(74) *Attorney, Agent, or Firm*—Hogan & Hartson LLP

(57) ABSTRACT

A plasticizer-free ion detective sensor for detecting a target ion in a sample is provided. The sensor comprises a copolymer of methacrylate monomers with pendant alkyl groups of different length, and an ionophore for detecting the target ion. The copolymer matrix of the present invention may be in a form of membrane or particles. The sensors of the present invention may be Carrier-based ion-selective electrodes (ISEs) or optodes such as thin film ion-specific optodes or particle-based optodes. The ionophore may be a target ionophore selective for a target ion $H^+$, $Li^+$, $Na^+$, $K^+$, $Ca^{2+}$, or $Mg^{2+}$. The ion detective sensor of the present invention may further include an ion exchanger such as halogenated carboranes. Also provided is an ion detective sensor comprising halogenated carboranes as ion exchangers. Particularly, trimethylammonium-2, 3, 4, 5, 6, 7, 8, 9, 10, 11, 12 undecabromocarborane (TMAUBC) is used as ion exchangers.

24 Claims, 12 Drawing Sheets

U.S. PATENT DOCUMENTS

| | | | | |
|---|---|---|---|---|
| 4,302,166 | A | | 11/1981 | Fulwyler et al. |
| 4,463,032 | A | * | 7/1984 | Arndt et al. ............... 427/222 |
| 4,507,425 | A | * | 3/1985 | Weaver ...................... 524/460 |
| 5,198,301 | A | * | 3/1993 | Hager et al. ........... 428/355 AK |
| 5,260,195 | A | * | 11/1993 | Azhar et al. ................. 435/25 |
| 5,644,069 | A | * | 7/1997 | Liu et al. ..................... 73/23.2 |
| 5,747,349 | A | | 5/1998 | van den Engh et al. |
| 6,143,558 | A | | 11/2000 | Kopelman et al. |
| 6,143,570 | A | * | 11/2000 | Alder et al. .................. 436/74 |
| 6,190,612 | B1 | * | 2/2001 | Berger et al. ............ 422/82.07 |
| 6,254,831 | B1 | * | 7/2001 | Barnard et al. .......... 422/82.08 |
| 6,277,330 | B1 | * | 8/2001 | Liu et al. ................. 422/82.05 |
| 6,548,310 | B1 | * | 4/2003 | Murata et al. ............... 436/518 |

FOREIGN PATENT DOCUMENTS

| | | | |
|---|---|---|---|
| EP | 0 490 631 A2 | | 6/1992 |
| JP | 57158202 | | 9/1982 |
| WO | 00/54039 | * | 9/2000 |

OTHER PUBLICATIONS

King, B. T. et al, Journal of the American Chemical Society 1996, 118, 3313-3314.*

Xie, Z. et al., Inorganic Chemistry 1998, 37, 6444-6451.*

Heng, L. Y. et al, Analytical Chemistry 2000, 72, 42-51.*

Heng, L. Y. et al, Analytical Chimica Acta 2000, 403, 77-89.*

Tsang, C.-W. et al, Inorganic Chemistry 2000, 39, 3582-3589.*

Telting-Diaz, M. et al, Analytical Chemistry 2001, 73, 5582-5589.*

Peper, S. et al, Analytical Chemistry 2002, 74, 1327-1332.*

"Production of Uniform Microspheres," The Review of Scientific Instruments (vol. 44—No. 2), Feb. 1973.

Bakker et al., "Plasticiser-Free Polymer Membrane Electrodes Containing a Methacrylic Copolymer Matrix" Electroanalysis, vol. 14, No. 19-20, 2002, pp. 1375-1381.

Rosatzin et al., "Preparation of Ca2+ Selective Sorbents by Molecular Imprinting Using Polymerisable Ionophores" Journal of Chemical Society, Perkin Transactions 2, No. 8, 1991, pp. 1261-1265.

Rosatzin et al., "Immobilization of Components in Polymer Membrane-Based Calcium-Selective Bulk Optodes," Analytical Checmistry, vol. 64, No. 18, 1992, pp. 2029-2035.

Schefer et al., "Neutral Carrier Based Ca2+ -Selective Electrode with Detection Limit in the Sub-Nanomolar Range," Analytical Chemistry, vol. 58, No. 11, Sep. 1986, pp. 2282-2285.

* cited by examiner

PLASTICIZER-FREE-ION-DETECTIVE SENSORS

RELATED APPLICANTS

The present invention claims priority to provisional application No. 60/337,099 filed on Dec. 6, 2001, entitled "Closo-Dodecacarboranes as Ion-exchangers in Cation-selective Chemical Sensors," and provisional application No. 60/337,101, filed on Dec. 6, 2001, entitled "Methyl Methacrylate-decyl Methacrylate as a Plasticizer-free Polymer Matrix for Ion-selective Sensing."

GOVERNMENT INTERESTS

The invention was made in the course of work supported by grants GM58589 and GM59716 from the National Institutes of Health. The United States government has certain rights in this invention.

BACKGROUND OF THE INVENTION

1. Area of the Art

The present invention is related to systems for detecting target ions in body fluids, and more specifically, it is related to plasticizer free ion sensors, and sensors containing ion exchangers.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Carrier-based ion-selective electrodes (ISEs) and optical sensors (optodes) have been used for detecting target ions in body fluids for many years. ISEs produce a measurable electrical change upon contact with a fluid sample containing target ions. Optodes, thin film ion-specific optodes or particle-based optodes, typically contain a target ionophore and an indicator ionophore. The target ionophore complexes with the target ion when present, and the indicator ionophore provides an indication of such complexing, such as by a color change.

Traditionally, poly(vinyl chloride) (PVC) has been the polymer matrix most commonly used in membrane-based ISEs and hydrophobic bulk optodes(1). This is primarily due to its high tensile strength, chemical inertness, and plasticizer compatibility(2).

There are several disadvantages, however, associated with the use of plasticized PVC in ion-selective sensors, one of which is plasticizer leaching (3). For in vivo measurements, where biocompatibility is of paramount importance, plasticizer leaching may result in a serious inflammatory response (4). Furthermore, leaching of plasticizers in biomedical devices has recently prompted the issuance of a health warning on biomaterials containing the common plasticizer bis(2-ethylhexyl) phthalate (DOP), and the commencement of an initiative to eliminate or reduce plasticizer content in such devices(5). With respect to ion determinations, exudation of plasticizer is one of the principle factors directly affecting sensor lifetime(6)(7). Moreover, a reduction in plasticizer content also results in an increased membrane resistance(6), and it may also decrease the solubility of the active sensing components within the membrane, thus causing a marked decrease in sensitivity and selectivity(8). These effects are expected to become more pronounced in miniaturized sensing platforms.

Miniaturized optodes that function in accordance with bulk extraction principles have typically been either fiber optic or particle-based. Optical fiber-based optodes are usually fabricated by immobilizing a sensing layer on the distal end of an optical fiber by a simple dip-coating procedure. Sensors of this type have been developed for several clinical analytes, including $H^+$,(9) $Cl^-$,(10) $Na^+$,(11) and $K^+$(12). Although this approach offers the advantages of reduced sample volume and high signal-to-noise ratio, it does not appear feasible for multiplexed analysis.

Particulate optodes have been produced by several different approaches, such as heterogeneous polymerization techniques(13)(14), solvent casting(15), and very recently with a high-throughput particle generator(16)(17). An obvious advantage of particulate optodes is their ability to independently interrogate a sample and produce a distinguishable analytical signal. To date, particle-based optodes have been used for very innovative applications, including flow cytometry(17) and intracellular monitoring(13)(18). The lifetime of these sensors, however, still remains a concern. In particulate probes used for intracellular measurements, lifetimes have been reported as short as 30 minutes(13), thus validating the need for methods that improve sensor lifetime.

One approach that has received a substantial amount of effort is the fabrication of plasticizer-free polymers. Several such polymers have been evaluated in ISEs or ion-selective field effect transistors (ISFETs), including polyurethanes (19), polysiloxanes(8)(10), silicone rubber(21)(22), polythiophenes(23), epoxyacrylates(24), and methacrylic(25) and methacrylic-acrylic copolymers(26)(28). Polymers synthesized via free radical initiated mechanisms, such as methacrylic-acrylic copolymers, appear quite attractive because of the numerous polymerization methods and infinite monomer combinations available to create polymers with a diverse range of physical and mechanical properties [29]. Hall and coworkers have done a substantial amount of work in this area (28 to 30, 78). Particularly, in PCT application WO 00/54039, Hall et al describe a selective polymer material with an acrylate backbone and a plurality of pendant lipophilic plasticising groups. Acrylate monomers are used to synthesize the polymers. The polymers are self-plasticising and thus are plasticizer free.

There are several disadvantages, however, to working with polymers containing acrylic monomers, including increased susceptibility to acid and base hydrolysis [30], inferior tensile strength [31], increased tacticity [30, 31], and malodorous vapor, all relative to their methacrylic counterparts. Therefore, a need still exists to develop a polymer matrix that would overcome the above-discussed disadvantages.

Carrier-based ion-selective electrodes (ISEs) and optical sensors (optodes) may also include ion-exchangers for improving their ion selectivities. Tetraphenylborate derivatives have been used as ion-exchangers in cation-selective solvent polymer membrane electrodes and bulk optodes for many years. They were initially introduced into ISE membranes to facilitate Donnan exclusion, which is the electrostatic repulsion of lipophilic anions trying to extract into the membrane(61). In addition to reducing anion interference, tetraphenylborates also decrease membrane resistance(62). It was later found that the presence of such borates in optimized concentrations improves ionophore selectivity by stabilizing the concentration of ion-ionophore complex(61).

The delocalized monoanionic charge that these compounds possess, in combination with their sterically hindered molecular structure make them very weakly coordinating. This is a characteristic that leads to weak, non-specific ion pair formation and maximum ionophore-mediated selectivity of the membrane(63).

Because the unsubstituted tetraphenylborate (TPB-) is susceptible to decomposition via acid hydrolysis, oxidants, and light, the search for more chemically stable derivatives began many years ago(61)(62)(64). The most successful derivative thus far has been the highly substituted 3,5[bis-(trifluoromethyl)phenyl]borate (NaTFPB)(65). The presence of strong electron-withdrawing groups decreases the tendency for cleavage of the boron-phenyl bond, because the amount of localized charge at the ipso carbons is significantly reduced(64). Furthermore, the presence of electron-withdrawing groups suppresses the π-coordination of the phenyl groups, thus making the compound more inert, and improving its electrochemical stability by increasing the reduction potential(64). Even though halogenated derivatives, such as NaTFPB, are more lipophilic and more resistant to phenyl cleavage, acid hydrolyzed decomposition still occurs albeit at a much slower rate(63)(65). This shortcoming limits the use of tetraphenylborates in systems requiring an acidic sample pH, as in the case of heavy metals, such as $Pb^{2+}$(66).

Compounds that may be suitable alternatives to tetraphenylborates are carboranes, specifically closo-dodecacarboranes. The chemical structure of the perbromo-substituted derivative appears in FIG. 8. These compounds possess many characteristics that may make them suitable ion-exchangers. Very weak ion pair formation is observed due to the lack of electron lone pairs and π-electrons, a property rarely found in anions(67). Moreover, as stated by Reed, the dodecacarborane anion, $CB_{11}H_{12}$, behaves "like a 3D analogue of benzene" because of the versatile functionalization chemistry that these compounds possess(67). The desired lipophilicity of this class of carboranes can easily be tailored both at the boron vertices(64)(69–71) and at the carbon vertex(70)(71). The most lipophilic derivatives that have been synthesized are those of the perhalogenated(68) and peralkylated dodecacarborane anion(69).

In addition to potentially unparalleled lipophilicity, the carboranes possess many other characteristics that make them suitable for electrochemical applications. For example, they are not susceptible to acid and base hydrolysis and they are relatively inert to electrochemical oxidation(~2.0 V vs. ferrocene/ferrocenium at Pt in dichloromethane)(67). High $I_h$ symmetry and tangentially delocalized σ-bonding make the carboranes one of the most chemically stable classes of compounds in chemistry. Furthermore, their bulky size (nearly 1 nm in diameter) and sufficient charge delocalization meet the criteria imposed for sufficient ion-exchanging. Another advantage, important for bulk optode studies, is their lack of absorption in the UV-Vis spectrum. Therefore, it is desirable to further study the carboranes for developing a more robust ion-exchanger to be used in chemical sensors.

SUMMARY OF THE INVENTION

One aspect of the present invention is directed to a plasticizer-free ion detective sensor for detecting a target ion in a sample. The sensor comprises a copolymer of methacrylate monomers with $R_1$ and $R_2$ pendant alkyl groups, and an ionophore for detecting the target ion; wherein $R_1$ is any of $C_{1-3}$ alkyl group, $R_2$ is any of $C_{4-12}$ alkyl group. In accordance with embodiments of the present invention, a copolymer of the present invention having a glass transitional temperature ($T_g$) of about or less than 0° C.

The copolymer matrix of the present invention may be in a form of membrane or particles. The sensors of the present invention may be Carrier-based ion-selective electrodes (ISEs) or optodes such as thin film ion-specific optodes or particle-based optodes. The ionophore may be a target ionophore selective for a target ion $H^+$, $Li^+$, $Na^+$, $K^+$, $Ca^{2+}$, or $Mg^{2+}$. The ion detective sensor of the present invention may also include an indicator ionophore such as a pH indicating chromoionophore, a chromoionophore, a fluoroionophore, a pH indicator, or a pH indicating fluoroionophore. The ion detective sensor of the present invention may further include an ion exchanger such as halogenated carboranes.

Another aspect of the present invention provides an ion detective sensor comprising halogenated carboranes as ion-exchangers. In accordance with embodiment of the present invention, the ion exchanges may be trimethylammonium-2, 3, 4, 5, 6, 7, 8, 9, 10, 11, 12 undecabromocarborane (TMAUBC). Similarly, in accordance with embodiments of the present invention, the ion detective sensor of the present invention may be a polymeric membrane electrode, a thin film bulk optode, or a particle-based optode.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

One aspect of the present invention is directed to a plasticizer-free ion detective sensor for detecting a target ion in a sample. A sensor of the present invention includes an ion-complexing agent (ionophore) and a copolymer matrix. The copolymer matrix is a copolymer of methacrylate monomers with different pendant alkyl groups $R_1$ and $R_2$, wherein $R_1$ may be any of $C_{1-3}$ alkyl group, and $R_2$ may be any of $C_{4-12}$ alkyl group.

It is a discovery of the present invention that polymers made with methacrylate monomers of different pendant alkyl groups provide unexpected advantages when compared with polymers made with acrylate monomers. Methacrylate polymers of the present invention provide higher glass transition temperature ($T_g$), and therefore have better mechanical strength. While not wanting to be bound by the theory, it is believed that the methacrylate monomer with longer pendant alkyl group may act as plasticizing components within the polymer, and the methacrylate monomer of shorter pendant alkyl group may provide the polymers with more rigid characteristics. Therefore, using methacrylate monomers of different pendant alkyl groups allows one to achieve a polymer material with not only a plasticizer-free effect but also a better mechanical strength for a desired $T_g$.

In addition, methacrylate polymers of the present invention are less sticky and therefore much easier to handle. This is particularly important when the polymer is used for particle-based ion detective sensors. Particles of ion detective sensors tend to stick together when acrylate polymers are used as a polymer matrix, whereas particles sensors having the polymer matrix of the present invention stay separate. Furthermore, the methacrylate monomers of the present invention have less of a characteristic smell, and thus are much easier to manufacture.

In accordance with embodiments of the present invention, preferably, $R_1$ is a $C_{1-2}$ alkyl group, and $R_2$ is a $C_{8-12}$ alkyl group. In one embodiment, methyl methacrylate and decyl methacrylate are used for forming a methyl methacrylate-decyl methacrylate (MMA-DMA) copolymer matrix of the present invention. Methacrylate monomers of the present invention are commercially available from, for example, Polysciences, Inc. (Warrington, Pa.).

Figure 2:
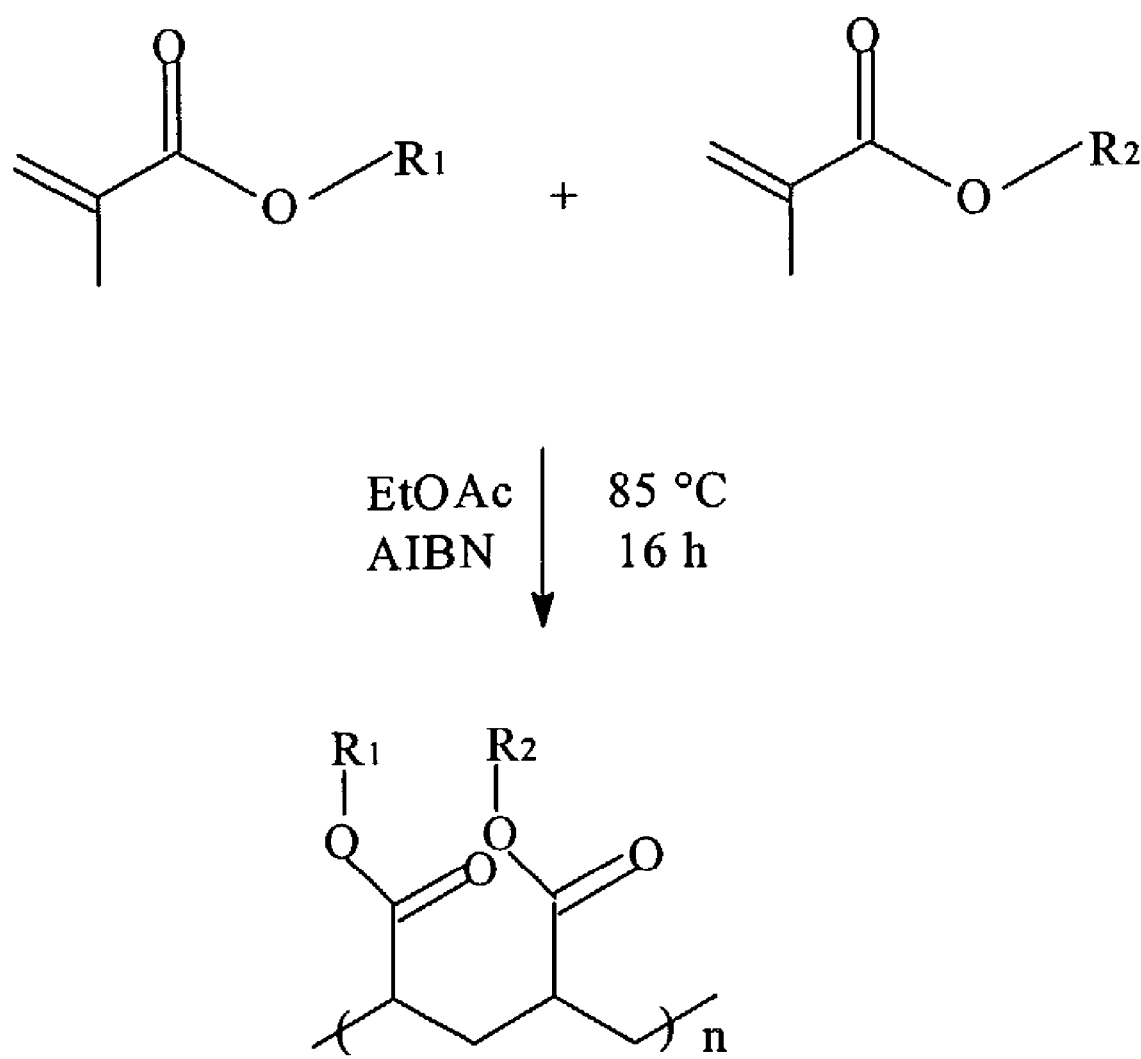
FIG. 2 is the free radical copolymerization reaction scheme of methyl methacryate (MMA) and decyl methacrylate (DMA) to give the desired non-crosslinked plasticizer-free ion-selective membrane material. The $R_1$ and $R_2$ groups denoted in the final structure are atactic methyl and decyl groups.

Copolymers of the present invention may be made in accordance with methods known in the art or the methods described herein in detail in the Examples. For example, copolymers of the present invention may be synthesized via thermally initiated free radical solution polymerization as described in the Examples I and II. One embodiment of the present invention as shown in FIG. 2 provides one reaction scheme for forming a copolymer of the present invention. In FIG. 2, $R_1$ and $R_2$ may be atactic methyl or decyl groups respectively.

The amount of each monomeric subunit needed to produce copolymers with a desired $T_g$ may be calculated using the Fox equation (see Equation 1). The $T_g$ is typically determined experimentally with a differential scanning calorimeter, a standard instrument for this purpose. Polymers with very low $T_g$ values are normally much softer and more difficult to handle mechanically. In accordance with the embodiments of the present invention, the $T_g$ of a copolymer may be about or below zero degrees Celsius. In one embodiment, the $T_g$ of a copolymer is in the range of between about 0 to −9° C. In another embodiment, the $T_g$ of a copolymer of the present invention is between about −5 to −8° C.

It is a discovery of the present invention that MMA-DMA copolymer matrix can be used to fabricate plasticizer-free ion-selective membranes or particles of an ion detective sensor. The ion detective sensors made of copolymer matrix of the present invention are plasticizer-free, and demonstrate superior or comparable ion selectivity when compared with polymer matrix made of bis(2-ethylhexyl sebacate) (DOS)-plasticized poly(vinyl chloride)(PVC) or DMA-DOS. The plasticizer-free ion detective sensor of the present invention allows the assessment of a wide variety of ions without experiencing the deleterious effects resulting from plasticizer leaching.

Methacrylate copolymer of the present invention may be used to fabricate the polymer matrix of a carrier-based ion-selective electrode (ISE), a thin film ion-specific optode, or a particle-based optode. For example, MMA-DMA copolymer may be used to fabricate polymer membranes of an ISE in accordance with methods described in Example I of the present invention or any other methods known to one skilled in the art. MMA-DMA copolymer may also be used to fabricate thin films to be used in a thin film ion-specific optode or to fabricate microsphere particles to be used in particle-based optodes in accordance with methods described in Example II of the present invention or any other methods know in the art.

Figure 5:
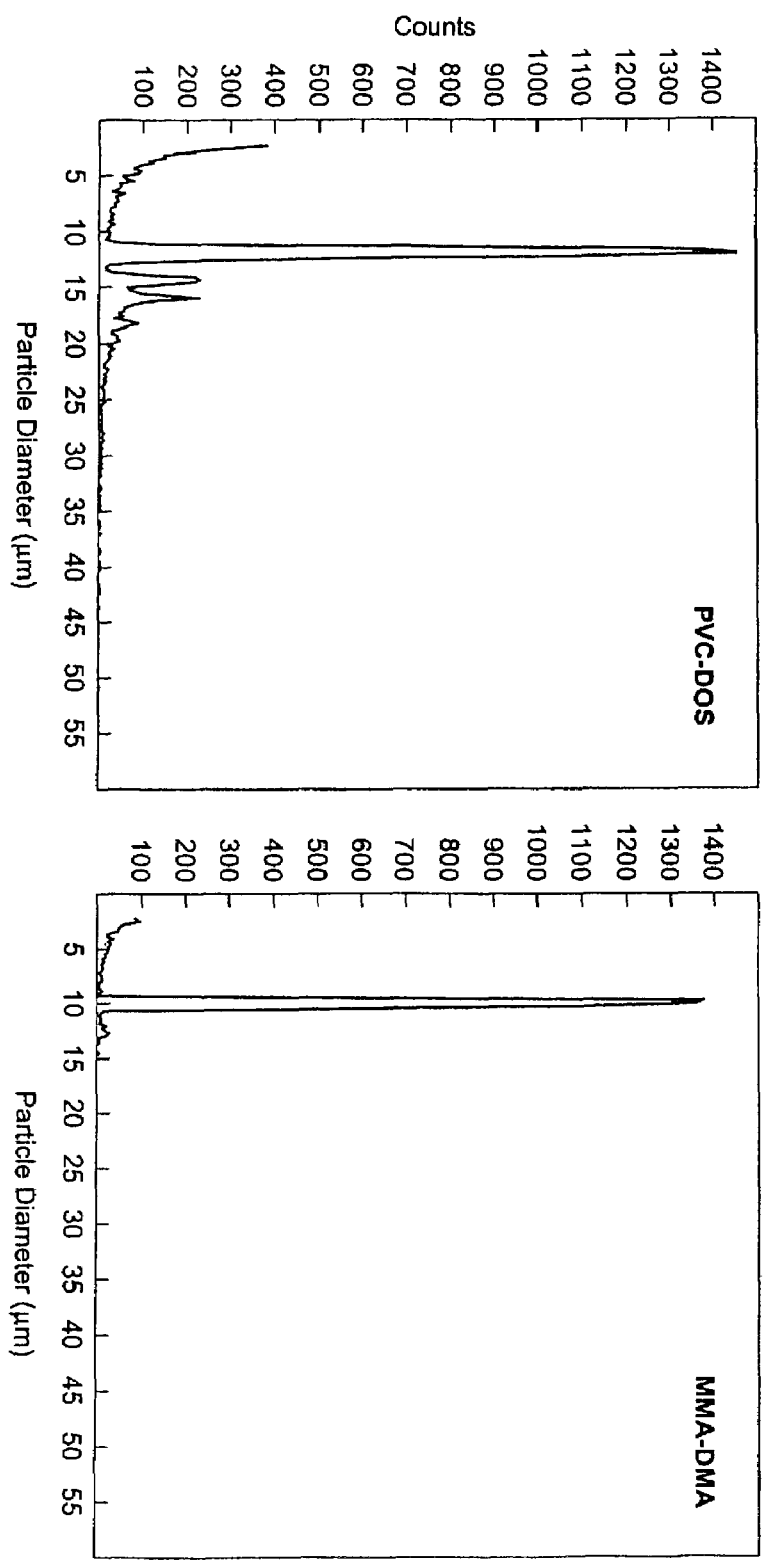
FIG. 5 shows sizing histograms of PVC-DOS (left) and MMA-DMA (right) microspheres. Mean particle diameter for PVC-DOS particles is 13.5±4.3 μm (N=10,470). Mean particle diameter for MMA-DMA particles is 10.0±0.9 μm (N=5452).

In accordance with one embodiment of the present invention, MMA-DMA copolymer of the present invention may be used to fabricate microsphere particles having an average diameter of the microspheres to be 10.0±0.9 µm (N=5452) over the particle range of 3 to 60 µm (see FIG. 5). One advantage that MMA-DMA particles have over PVC-DOS particles fabricated using the same procedure is their lack of coalescence during the casting and/or curing processes. The histograms in FIG. 5 show no signs of particle agglomeration for the particles made with MMA-DMA (right), which can be deduced by the absence of doublet and triplet particle distributions often seen in analogous particles made with PVC-DOS (left). This lack of coalescence, in combination with a very narrow size distribution, makes MMA-DMA microspheres suitable for incorporation into several popular sensing platforms, including lab-on-a-chip technologies, bundled optical fiber arrays, micro-well plate-format assays, and flow cytometry.

Figure 1:
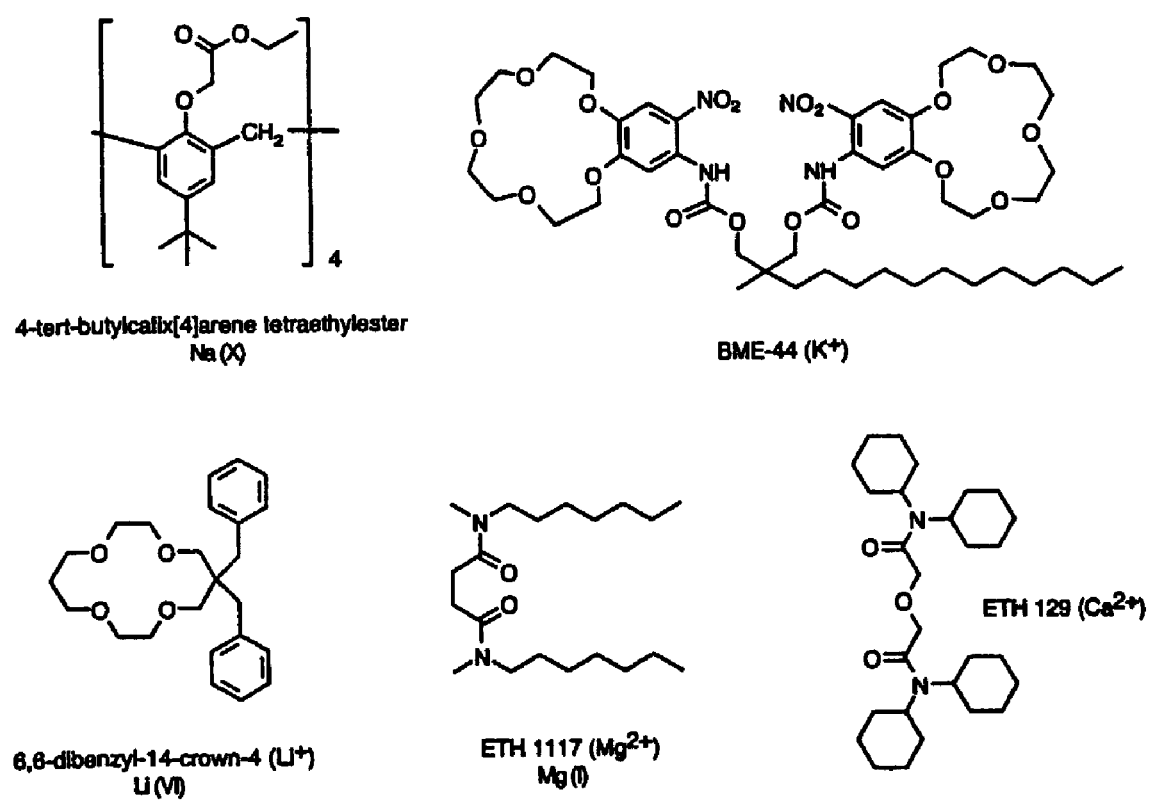
FIG. 1 shows chemical structures of the five studied ionophores.

The copolymer matrix of the present invention may be used in connection with a wide variety of ionophores for detecting different target ions. Examples of such ionophores include, but not are limited to, ionophores selective for a target ion $H^+$, $Li^+$, $Na^+$, $K^+$, $Ca^{+2}$, or $Mg^{2+}$. FIG. 1 shows the structures of different ionophores of the present invention that may be used for detecting different target ions.

When the plasticizer-free ion detective sensor of the present invention is in a form of optodes, the sensor further includes an indicator ionophore. Examples of indicator ionophore include, but are not limited to, a pH indicating chromoionophore, a chromoionophore, a fluoroionophore, a pH indicator, or a pH indicating fluoroionophore.

It should be appreciated that the ion detective sensor of the present invention may include a plurality of target ionophores and indicator ionophores for detecting different target ions at the same time. Generally, the two ionophores are different molecules. However, in accordance with the embodiments of the present invention, it is possible to utilize a compound in which the indicator ionophore and the target ionophore are coupled into a single molecule. An example of such a molecule is described in U.S. Pat. No. 6,165,796, the relevant content of which is incorporated herein by reference.

The ion detective sensors of the present invention may also include other additives such as ion-exchangers to enhance the extraction of the target ion from the aqueous sample and the migration of the target ion into the polymer matrix. While any ion exchangers that provide lipophilic anionic sites on the polymer matrix may be used, preferably, carba-closo-dodecaborates, particularly halogenated carborane anions, are used as ion exchangers.

It is a discovery of the present invention that halogenated carboranes demonstrated excellent stability, lipophilicity, and suitable electrostatic properties when used as ion exchangers with ion detective sensors, particularly when used as ion exchangers in a non-traditional sample conditions, including strongly acidic media. Accordingly, another aspect of the present invention provides an ion detective sensor comprising halogenated carboranes as ion exchangers.

Figure 8:
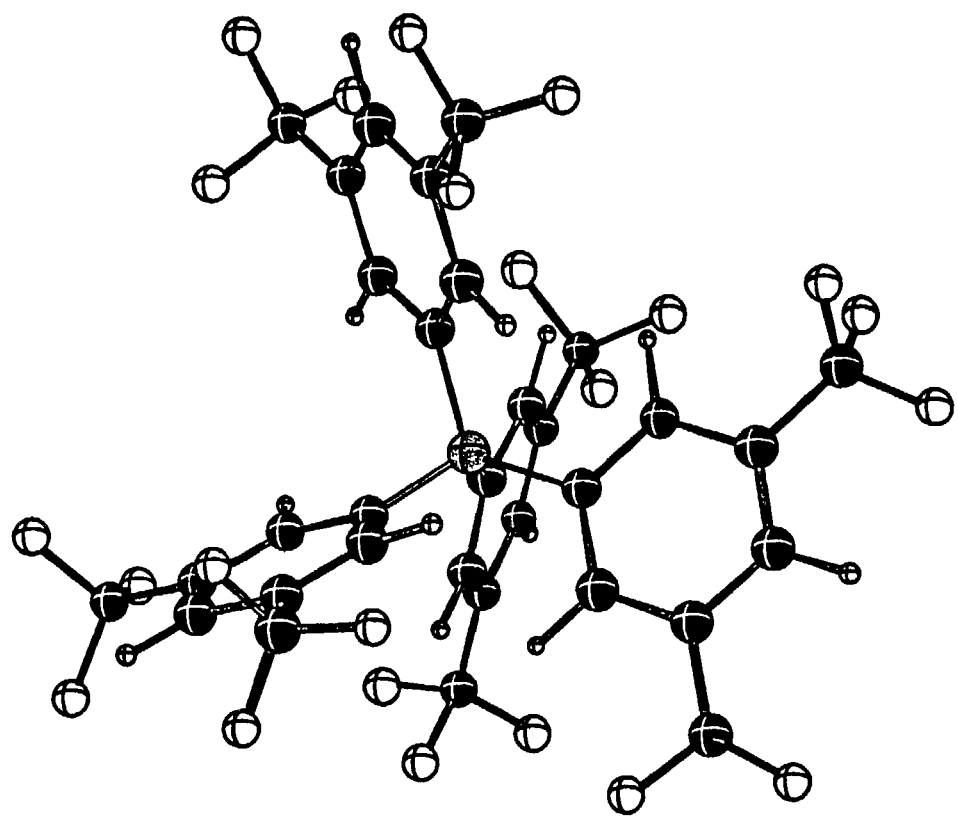
FIG. 8 shows three-dimensional chemical structures of the ion-exchangers of the present invention. Left: 3,5[bis-(trifluoromethyl)phenyl]borate (TFPB-); Right: perbrominated closo-dodecacarborane anion, 1-$HCB_{11}Br_{11}$— (UBC-).
Figure 8:
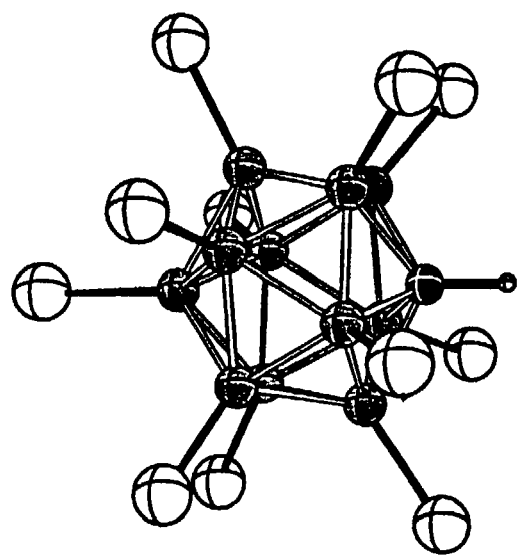

In one embodiment of the present invention, trimethylammonium-2, 3, 4, 5, 6, 7, 8, 9, 10, 11, 12 undecabromocarborane (TMAUBC) is used as ion exchangers of the sensors of the present invention. FIG. 8 shows the three-dimensional chemical structure of perbrominated closo-dodecacarborane anion, 1-$HCB_{11}Br_{11}$—(UBC-). TMAUBC may be synthesized by the methods known in the art or in accordance with the methods described in Example III of the present invention. TMAUBC may be used as ion exchangers in solvent polymeric membrane ion-selective electrodes or bulk optodes of the present invention.

Alternatively, other halogenated carboranes may also be used as ion exchangers of the present invention. Examples of such halogenated carboranes include, but are not limited to, undecachlorinated (UCC), hexabrominated (HBC) and undecaiodinated (UIC) carborane anions.

The ion detective sensors of the present invention may be used for detecting ions of all types of body fluid samples. Examples of the samples include, but are not limited to, whole blood, spinal fluid, blood serum, urine, saliva, semen, tears, etc. The fluid sample can be assayed neat or after dilution or treatment with a buffer.

The following examples are illustrative of the present invention.

EXAMPLE I

Plasticizer-Free Ion-Selective Sensors Containing Membranes made of MMA-DMA

Reagents: The monomers methyl methacrylate, 99.5%, (MMA) and n-decyl methacrylate, 99%, (DMA) were obtained from Polysciences, Inc. (Warrington, Pa.). The polymerization initiator 2,2'-azobis(isobutyronitrile), 98%, (AIBN) was obtained from Aldrich. Ethyl acetate, and 1,4-dioxane were reagent grade and obtained from Fisher. Inhibitors were removed from the monomers by washing with a caustic solution containing 5% (w/v) NaOH & 20% NaCl in a 1:5 (monomer:caustic solution) ratio. This purification process has previously been reported [29]. After inhibitor removal, the monomers were rinsed with an excess of water, treated with anhydrous $Na_2SO_4$, and filtered before use. AIBN was recrystallized from warm methanol prior to use.

The ionophores [4-tert-butylcalix[4]arene-tetraacetic acid tetraethyl ester] (Na (X)), [2-dodecyl-2-methyl-1,3-propanediylbis [N-[5'-nitro(benzo-15-crown-5)-4'-yl]carbamate]]] (K(III), BME-44), [6,6-dibenzyl-14-crown-4 (Li(VI)), [N,N'-diheptyl-N,N',dimethyl-1,4-butanediamide] (Mg (I), ETH 1117) and [N,N,N',N'-tetracyclohexyl-3-oxapentanediamide] (Ca (II), ETH 129) were Selectophore™ quality from Fluka (Milwaukee, Wis.). The ion-exchangers, sodium tetrakis[3,5-bis(trifluoromethyl)phenyl]borate (NaTFPB) and tridodecylmethylammonium chloride (TDMAC), were purchased in the highest quality available from Fluka. All aqueous solutions were prepared with Nanopure® (18.2 MΩ cm) deionized water from the chloride salts of the alkali and alkaline earth metals studied.

Polymer synthesis: Methacrylic copolymers were synthesized via thermally initiated free radical solution polymerization (see FIG. 2 for reaction scheme). The amount of each monomeric subunit needed to produce copolymers with a glass transition temperature ($T_g$) of −5° C. was calculated using the Fox equation (see Eqn. 1). The use of the Fox equation for calculating weight fractions of copolymers has previously been reported [31,32]. The calculated amounts of each monomeric unit were added to 5 ml of dry ethyl acetate. The solution was purged with $N_2$ for 10 minutes before adding 3.4 mg of AIBN. The homogeneous solution was continuously stirred and the temperature was ramped to 85° C., which was maintained for 16 h. After the reaction was complete, the solvent was evaporated and the polymer was redissolved in 10 ml of dioxane. The polymer solution was added dropwise to 800 ml of distilled water under vigorous stirring. The white precipitate was collected and dissolved in 25 ml of methylene chloride, followed by water removal with anhydrous $Na_2SO_4$ and filtering. The solvent was evaporated and the transparent polymer was air dried.

Membrane Preparation and Measurement: Polymer membranes were prepared by dissolving 20 mmol/kg ionophore, 5 mmol/kg ionic sites and copolymer in 1.5 ml of methylene chloride. The total weight of the cocktail was 200 mg. The membrane cocktail was poured into a glass ring (22 mm i.d.) affixed onto a glass slide. The solvent was evaporated overnight to give a transparent membrane with a thickness of about 200 μm. The membrane was soaked in water for an hour and carefully peeled from the glass slide with a scalpel. The membranes were either conditioned in 0.01 M $MgCl_2$ or LiCl (for Mg (I) based membranes) solutions overnight [35]. Discs 6 mm in diameter were cut from the parent membranes and mounted into Philips electrode bodies (IS-561, Glasbläserei Möller, Zurich, Switzerland). A 0.01 M $MgCl_2$ or LiCl (for Mg (I) based membranes) solution was used as the inner filling solution. Potentiometry measurements were performed at laboratory ambient temperature in unstirred solutions versus a Ag/AgCl reference electrode containing a 1 M LiOAc electrolyte bridge.

Results and Discussion

In years past, homopolymers made from methyl methacrylate (MMA) and decyl methacrylate (DMA) monomers have been evaluated as ISE matrices. Due to plasticizer incompatibility, poly(MMA) proved to be an unsuitable matrix [33], while plasticized poly(DMA), however, was successfully used in several types of ISEs [34,36] and bulk optode films [34,35]. Nonetheless, because of the poor mechanical stability of poly(DMA), sensing membranes could only be made from cross-linked photopolymerized polymers that required the use of an additional plasticizer. Photoinitiated bulk polymerization processes yield polymers with very high molecular weight distributions, which increases the tensile strength of the polymer produced [30, 31].

By using the Fox equation, which allows one to calculate an approximate $T_g$ of a copolymer based on the weight fractions and glass-transition temperatures of the respective monomers, a copolymer may be produced that has characteristics of both monomers. The Fox equation appears as Equation 1 [31, 32]

$$\frac{1}{T_g(co)} = \frac{F_A}{T_g(A)} + \frac{F_B}{T_g(B)} \quad (1)$$

where $F_A$ and $F_B$ are the weight fractions of each monomer, $T_g(A)$ and $T_g(B)$ are their glass-transition temperatures in Kelvin, and $T_g(co)$ is the calculated glass-transition temperature of the resulting copolymer in Kelvin. The use of this equation to produce copolymers from methacrylic and acrylic esters has previously been reported by Hall et al. [32].

The present invention reports the first methacrylic copolymer prepared from MMA and DMA for use in ion-selective sensing membranes. The glass-transition temperatures of homopolymers made from these monomers are 105° C. and −30° C., respectively. The presence of DMA improves the film-forming properties of the polymer, while that of DMA reduces the glass-transition temperature, thus acting as a so-called internal plasticizer. Using Eq. 1, a polymer with a calculated $T_g$ of −5° C. was produced. This calculated value correlates well with the experimental $T_g$ of −8° C. determined using differential scanning calorimetry (DSC). A calculated $T_g$ of −5° C. was selected because the copolymer produced using the respective weight fractions of each monomer had the most favorable mechanical properties. This observation concurs with the findings of Malinowska and coworkers that optimal mechanical properties of a methyl methacrylate isodecyl acrylate copolymer (MMA-IDA) lie within the range of −10° C. to 10° C.

It is well known that plasticizers and PVC both contain native anionic sites [1]. The impurities found in PVC are residual from the manufacturing process [1]. This is the reason why plasticized PVC membranes containing only an ionophore can give a Nernstian, cation response. In contrast, an ISE membrane composed of only MMA-DMA copolymer produced a very noisy signal and no response to sample ions (data not shown). This suggests that the polymer contains a very low amount of ionic impurities and that the blank copolymer membranes have a relatively high resistance, which is in agreement with the literature [32]. Indeed, one of the reasons that homogeneous solution polymerization was selected as the synthetic method was that this technique produces polymers with very little ionic impurities [29–31].

Figure 3:
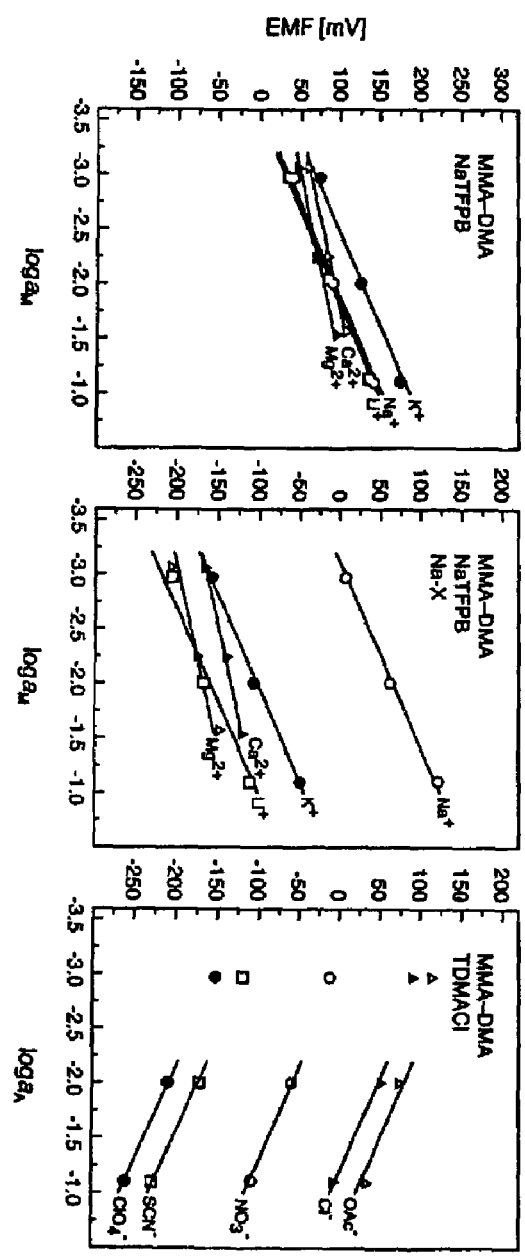
FIG. 3 are diagrams which show separate solution potentiometric response functions of ion-selective electrode membranes based on plasticizer-free MMA-DMA, containing either the cation-exchanger NaTFPB (left), NaTFPB and the sodium ionophore Na (X) (middle), or the anion-exchanger TDMAC (right).

Polymer membranes doped with 10 mmol/kg anionic (NaTFPB) or cationic sites (TDMAC) have been evaluated potentiometrically (see FIG. 3). The resulting membranes were clear and homogeneous. The plasticizer-free membranes had response times comparable to those of plasticized PVC membranes and they exhibited Nernstian responses towards all of the ions measured. This indicates that ion-exchange processes in MMA-DMA copolymer membranes are similar to those found in plasticized PVC membranes. The selectivity pattern observed with the copolymer membrane is the same as that demonstrated by plasticized PVC (see Table 1 and FIG. 3). In ionophore-free membranes selectivity is dictated by the hydration enthalpies of the sample ions. The MMA-DMA membrane showed the same potassium-sodium selectivity as the PVC-DOS membrane while the selectivity over $Mg^{2+}$ and $Ca^{2+}$ was between that of PVC-DOS and poly(vinyl chloride) plasticized with o-nitrophenyl octyl ether (PVC-NPOE). This result may be related to the structure and electronic properties of the copolymer. Methyl methacrylate and decyl methacrylate form linear copolymers with numerous pendant ester moieties, which is structurally similar to the plasticizer DOS. It has been reported earlier that the carbonyl groups found in DOS can bind cations [42], so it seems plausible that DOS is capable of behaving as an ionophore in these cases. The abundant ester groups in the MMA-DMA matrix may be interacting with small cations in a very similar fashion. The dielectric constant for poly(methyl methacrylate) (PMMA) is low ($\epsilon$=3) [43], and similar to DOS. The magnitude of the dielectric constant of an ISE membrane has been shown to affect the divalent/monovalent ion selectivity ratio [44], although this rule of thumb does not apply to all membrane matrices [45]. In membranes with high dielectric constants, such as PVC-NPOE ($\epsilon$=24), there is often some preference for divalent cations. The slopes and selectivity coefficients of the anion exchanger TDMAC based copolymer membranes are also shown in Table 1 and are visualized in FIG. 3. The copolymer membrane exhibited the expected Hofmeister selectivity pattern, in which more lipophilic anions are preferred. The TDMAC based MMA-DMA membrane demonstrated selectivity comparable to the plasticized PVC membranes, although here the less lipophilic acetate anion gave a sub-Nernstian response slope.

The observed response of the ion exchanger-based copolymer membranes indicated that the compatibility of the ion exchangers in the polymer matrix is good and that the extraction of sample ions in the polymer membrane is sufficiently rapid. However, the applications of a plasticizer-free polymer matrix are limited not only by its physical and mechanical properties, but also by the compatibility and solubility of the ionophores used in the membrane material. To demonstrate that MMA-DMA is a suitable matrix for ISEs, several different cation-selective ionophores were evaluated using MMA-DMA. A broad investigation of different ionophore-based plasticizer-free polymer membrane ISEs has not been presented previously. In the present invention, ionophores of five metal cations were tested using the MMA-DMA polymer as membrane material. The structures of these ionophores appear in FIG. 1.

TABLE 1

SELECTIVITY COMPARISON OF IONOPHORE-FREE ION EXCHANGER MEMBRANES CONTAINING EITHER MMA-DMA OR PLASTICIZED PVC.

| | Membranes containing NaTFPB | | |
|---|---|---|---|
| | MMA-DMA | PVC-DOS[a] | PVC-NPOE[b] |
| Ion J: | slope [mV/dec] Log $K_{K,J}^{pot}$ | log $K_{K,J}^{pot}$ | log $K_{K,J}^{pot}$ |
| $Mg^{2+}$ | 29.6 ± 3.1    −1.9 ± 0.3 | −2.6 | −1.1 |
| $Ca^{2+}$ | 32.5 ± 2.5    −1.6 ± 0.3 | −2.6 | −0.5 |
| $Li^+$ | 53.7 ± 1.3    −0.6 ± 0.1 | | |

TABLE 1-continued

SELECTIVITY COMPARISON OF IONOPHORE-FREE ION EXCHANGER MEMBRANES CONTAINING EITHER MMA-DMA OR PLASTICIZED PVC.

| $Na^+$ | 55.1 ± 3.5    −05. ± 0.1 | −0.5 | −1.2 |
|---|---|---|---|
| $K^+$ | 54.2 ± 2.3    0 | 0 | 0 |
| | Membranes containing TDMAC | | |
| | MMA-DMA | PVC-DOS[c] | PVC-NPOE[d] |
| Ion J: | slope [mV/dec]    Log$K_{Cl,J}^{pot}$ | log $K_{Cl,J}^{pot}$ | log $K_{Cl,J}$ |
| OAc— | −43.2 ± 4.3    −0.7 ± 0.1 | | |
| Cl— | −52.6 ± 0.9    0 | 0 | 0 |
| $NO_3$— | −52.0 ± 1.4    1.9 ± 0.1 | 1.9 | 2.1 |
| SCN— | −57.8 ± 1.1    2.8 ± 0.1 | 3.6 | 3.8 |
| $ClO_4$— | −57.5 ± 1.7    4.3 ± 0.2 | 4.8[c] | 5.1[c] |

[a]From [49].
[b]From [50].
[c]From [43].

The response slopes and selectivity behavior observed using the sodium-selective calixarene, Na (X), dissolved in MMA-DMA are shown in FIG. 3 and compared with various other plasticizer-free matrices in Table 2. By conditioning the electrodes in an interfering ion, Nernstian or nearly Nernstian response slopes were achieved for both interfering ions and the primary ion [38,39]. This made it possible to calculate unbiased selectivities using the separate solution method. MMA-DMA membranes showed a Nernstian response range from $10^{-5}$ to $10^{-1}$ M $Na^+$. As shown in Table 2, the MMA-DMA membrane gave better selectivities than PVC-DOS and PVC-NPOE membranes in many cases, and proved to be superior when compared to other plasticizer-free matrices, such as MMA-DMA and silicone rubber. These data indicate that Na(X) has good compatibility with the MMA-DMA copolymer. The chemical structure of Na (X) shows several flexible carbonyl groups inside the ring that form a cavity suitable for binding $Na^+$, and a tert-butyl group on the upper rim to maintain the rigidity of the molecule. The ester groups in the copolymer matrix may interact with the carbonyl groups of the ionophore and make the cavity more rigid and potentially more suitable for binding sodium, and thus increasing the $Na^+$ selectivity over other metal ions. $Li^+$ demonstrated a sub-Nernstian response with the calixarene ionophore. This may be due to the high hydration enthalpy and smaller ionic radius of $Li^+$, which may make it more difficult to displace the conditioning ion, $Mg^{2+}$, from the membrane.

TABLE 2

EXPERIMENTAL SELECTIVITY COEFFICIENTS LOG $K_{Na,J}^{pot}$ OF MEMBRANES CONTAINING THE SODIUM IONOPHORE Na (X).

| Ion J: | MMA-DMA | PVC-DOS[a] | PVC-NPOE[b] | MMA-IDA[c] | silicone rubber[d] |
|---|---|---|---|---|---|
| $Mg^{2+}$ | 30[e] ± 1    −4.3 ± 0.1 | −4.3 | <−6 | −3.8 | |
| $Ca^{2+}$ | 28.6 ± 0.7  −4.9 ± 0.1 | −4.0 | −2.5 | −3.6 | −4.1 |
| $Li^+$ | 45.6 ± 0.4  −3.8 ± 0.1 | | −2.5 | | |
| $K^+$ | 56.9 ± 0.1  −2.8 ± 0.1 | −2.0 | −1.9 | −2.0 | −2.8 |
| $Na^+$ | 58 ± 2    0 | 0 | 0 | 0 | 0 |

[a]From [28].
[b]From [51].
[c]From [28].
[d]From [54].
[e]electrode slope in mV decade$^{-1}$.

Table 3 shows the response slopes and selectivity behavior of other ionophores evaluated in the copolymer membrane. BME-44, a bis-crown ether, is a potassium-selective ionophore. The selectivities found with this ionophore in MMA-DMA membranes are somewhat inferior to those observed for PVC-DOS and PVC-NPOE membranes, especially for $Li^+$. It has been reported that selectivity coefficients of polar NPOE membranes are usually much smaller than those of non-polar dipentyl phthalate (DPP) or DOS systems in crown ether-based membranes [40]. Although the MMA-DMA copolymer has ester groups, they are not sufficient to induce high polarity. Perhaps for this reason, as well as the long alkyl chains in the polymer structure, membranes made from MMA-DMA copolymer behave more like non-polar PVC-DOS membranes rather than NPOE membranes. Another crown ether type ionophore, Li (VI), also showed inferior selectivity in MMA-DMA membranes, presumably for the same reason discussed above. The substituted diamide Mg (I) showed a significantly worse magnesium selectivity than in PVC-NPOE membranes (see Table 3). However, it seems that this is not due to an incompatibility of the ionophore in this matrix, since it showed better selectivity than the PVC-DOS membrane under otherwise exactly the same conditions (Table 3). The inferior selectivity in these two matrices may be due to the ester groups in the copolymer and plasticizer, which may interact with the oxygen atoms in the ionophore and make the single bond between the carbon and oxygen rotate. This could result in a loss of binding affinity for $Mg^{2+}$. On the other hand, the ester groups may compete with the ionophore, thus rendering the ion extraction less selective. The selectivity of amide-type calcium ionophore ETH 129 is similar to the established literature (Table 3), but inferior to the unbiased selectivity data reported recently [35]. Although the selectivity of the carrier based MMA-DMA copolymer membranes is somewhat inferior to plasticized PVC membranes in some cases, it appears to be generally suitable for blood electrolyte measurements [41].

TABLE 3

EXPERIMENTAL SELECTIVITY COEFFICIENTS FOR MEMBRANES CONTAINING OTHER IONOPHORES.

Membranes containing BME-44 ($K^+$)

| | MMA-DMA | | PVC-DOS | PVC-NPOE |
|---|---|---|---|---|
| Ion J: | slope [mV/dec] | $\log K_{K,J}^{opt}$ | $\log K_{K,J}^{opt}$ | $\log K_{K,J}^{opt}$ |
| $Mg^{2+}$ | 29.4 ± 0.9 | −3.9 ± 0.1 | | −4.4[b] |
| $Ca^{2+}$ | 28.9 ± 2.8 | −3.9 ± 0.2 | −4.2[a] | −4.6 |
| $Li^+$ | 43.9 ± 1.7 | −2.5 ± 0.4 | −3.8 | −3.6 |
| $Na^+$ | 53.2 ± 0.5 | −2.8 ± 0.2 | −3.2 | −3.1 |
| $K^+$ | 58.8 ± 0.8 | 0 | 0 | |

Membranes containing Li(VI)

| | MMA-DMA | | PVC-DOS[a] | PVC-NPOE[b] |
|---|---|---|---|---|
| Ion J: | slope [mV/dec] | $\log K_{Li,J}^{opt}$ | $\log K_{Li,J}^{opt}$ | $\log K_{Li,J}^{opt}$ |
| $Mg^{2+}$ | 26.8 ± 3.4 | −3.4 ± 0.3 | −4.6[c] | −4.8[c] |
| $Ca^{2+}$ | 30.6 ± 2.1 | −2.9 ± 0.2 | −4.4 | −4.3 |
| $K^+$ | 53.7 ± 3.1 | −1.5 ± 0.1 | −1.9 | −2.3 |
| $Na^+$ | 55.5 ± 2.0 | −2.4 ± 0.5 | −1.9 | −2.4 |
| $Li^+$ | 60.4 ± 0.4 | 0 | 0 | 0 |

Membranes containing Mg(I)

| | MMA-DMA | | PVC-DOS | PVC-NPOE |
|---|---|---|---|---|
| Ion J: | slope [mV/dec] | $\log K_{Mg,J}^{opt}$ | $\log K_{Mg,J}^{opt}$ | $\log K_{Mg,J}^{opt}$ |
| $Ca^{2+}$ | 29.3 ± 3.3 | 1.3 ± 0.3 | 0.9 | −1.5[d] |
| $K^+$ | 51.6 ± 7.2 | 0.7 ± 0.2 | 1.6 | −1.2 |
| $Na^+$ | 38.9 ± 5.9 | 0.3 ± 0.2 | 1.4 | −2.3 |
| $Li^+$ | 51.7 ± 3.8 | 0.9 ± 0.3 | 1.7 | −0.9 |
| $Mg^{2+}$ | 30.4 ± 0.9 | 0 | 0 | 0 |

Membranes containing ETH 129 ($Ca^{2+}$)

| | MMA-DMA | | PVC-DOS | PVC-NPOE |
|---|---|---|---|---|
| Ion J: | slope [mV/dec] | $\log K_{Ca,J}^{opt}$ | $\log K_{Ca,J}^{opt}$ | $\log K_{Ca,J}^{opt}$ |
| $Mg^{2+}$ | 28.9 ± 2.8 | −5.4 ± 0.2 | −4.9[e] | −4.6[e] |
| $Li^+$ | 50.7 ± 4.6 | −3.8 ± 0.5 | | −3.3 |
| $K^+$ | 54.6 ± 6.5 | −4.1 ± 0.4 | −4.0 | −3.8 |
| $Na^+$ | 51.4 ± 2.1 | −4.7 ± 0.4 | −3.6 | −3.7 |
| $Ca^{2+}$ | 28.8 ± 3.1 | 0 | 0 | 0 |

Conclusions

The MMA-DMA copolymer of the present invention is the first methacrylate copolymer to be used in ion-selective electrodes. Its good mechanical and adhesive properties make it suitable for fabricating plasticizer-free ion-selective membranes by traditional solvent casting. The ionophore based polymer membrane showed Nernstian response slopes and comparable selectivity to conventional PVC membranes. The copolymer membrane behaves much like PVC-DOS membranes due to it similar structure rich in ester groups.

EXAMPLE II

Plasticizer-free Ion Selective Optodes Made of MMA-DMA Copolymer

Reagents. Polymer Synthesis. The monomers methyl methacrylate, 99.5%, (MMA) and n-decyl methacrylate, 99%, (DMA) were obtained from Polysciences, Inc. (Warrington, Pa.). The polymerization initiator 2,2'-azobis(isobutyronitrile) (AIBN), 98%, was obtained from Aldrich. Ethyl acetate, dichloromethane 1,4-dioxane, and anhydrous $Na_2SO_4$ were reagent grade from Fisher and used as received.

Particle and Film Preparation. The ionophore [2-dodecyl-2-methyl-1,3-propanediylbis[N-[5'-nitro(benzo-15-crown-5)-4'-yl]carbamate]]](potassium ionophore III, BME-44), the chromoionophore [9-(diethylamino)-5-octadecanoylimino-5H-benzo[a]phenoxazine](chromoionophore I, ETH 5294), and tetrahydrofuran (THF) were Selectophore™ quality from Fluka (Milwaukee, Wis.). Sodium tetrakis(3,5-bis(trifluoromethyl)phenyl borate (NaTFPB) was obtained in the highest purity available from Dojindo Laboratories (Gaithersburg, Md.). Poly(ethylene glycol) (PEG: MW 600) was purchased from Polysciences and polyoxyethylene sorbitanmonolaureate (Tween 20) was obtained from Fluka. Citric acid monohydrate, boric acid, sodium phosphate monobasic, hydrochloric acid, nitric acid, sodium hydroxide, sodium salts of chloride, nitrate, and perchlorate, and chloride salts of potassium, calcium, and magnesium were purchased from Fluka. N-[2-hydroxyethyl] piperazine-N'-[2-ethanesulfonic acid] (HEPES) was purchased from Sigma-Aldrich (St. Louis, Mo.). All aqueous solutions were prepared with Nanopure® (18.2 MΩ cm) deionized water.

Polymer Synthesis. Inhibitors were removed from the monomers in accordance with a previously described protocol[56] by washing with a caustic solution containing 5% (w/v) NaOH & 20% (w/v) NaCl in a 1:5 (monomer:caustic solution) ratio. After inhibitor removal, the monomers were rinsed with an excess of water, treated with anhydrous $Na_2SO_4$, and filtered before use. Prior to use AIBN was recrystallized from warm methanol.

(Synthesis of Polymer 1) A quantity of 1.06 g of MMA and 3.94 g of DMA were added to 15 mL of ethyl acetate in a 25 mL round-bottom flask. The solution was purged with $N_2$ for 15 minutes prior to adding 10.2 mg of AIBN. The flask containing the homogeneous solution was immersed in an oil bath that was preheated to 85° C. and continuously stirred at that temperature under an $N_2$ atmosphere for 18 h. After the reaction was complete, the ethyl acetate was evaporated off and the polymer was dissolved in 20 mL of dioxane. This solution was added dropwise to 800 mL of deionized water under vigorous stirring. The White precipitate that formed was collected and dissolved in 40 mL of dichloromethane, followed by water removal with anhydrous $Na_2SO_4$ and filtering. The dichloromethane was evaporated under ambient laboratory conditions producing an elastomeric transparent polymer.

(Synthesis of Polymer 2) A quantity of 1.06 g of MMA and 3.94 g of DMA were added to 20 mL of ethyl acetate in a 25 mL round-bottom flask. The solution was purged with $N_2$ for 15 minutes prior to adding 20.0 mg of AIBN. The reaction flask was immersed in an oil bath that was preheated to 60° C. and continuously stirred at that temperature under an $N_2$ atmosphere for 24 h. Polymer recovery and purification was carried out according to the procedure mentioned above. Reaction conditions are similar to those previously reported by Mohr et al. (54)

Thin Film Preparation. Cocktails for coextraction studies consisted of 10 mmol/kg ETH 5294 and MMA-DMA (1) (300 mg total weight) dissolved in 1.75 mL THF. For ion-exchange studies, sensing cocktails (350 mg total weight) contained 6.4 mmol/kg ETH 5294, 30.4 mmol/kg BME-44, 15.2 mmol/kg NaTFPB and MMA-DMA (2) dissolved in 2 mL THF. A 200 µL aliquot of cocktail was used to cast films onto quartz disks using a spin-coating device previously described(56). The freshly prepared films were dried in ambient air for at least 2 h prior to use.

Particle Preparation. Particles were prepared using a particle casting apparatus that has previously been described (16). To summarize, a sensing cocktail (55 mg total weight) containing either MMA-DMA (1) and ETH 5294 only or MMA-DMA (2), BME-44, ETH 5294, and NaTFPB (in the same concentrations used for thin films) was dissolved in 30 mL of dichloromethane and filtered with a 0.45 µm syringe filter. In contrast to the previous report, the polymer solution was directed by a syringe pump (Stoelting Co., Wood Dale, Ill.), while an aqueous sheath liquid (deionized water) was hydrostatically directed from a storage bottle into a mixing chamber. The polymer cocktail enters the proximal end of the mixing chamber assembly where it is directed towards a ceramic orifice of fixed diameter located at the distal end of the assembly. By adjusting the operating frequency of a piezoelectric transducer that is mounted on the proximal end of the assembly, the polymer stream is broken off into uniform droplets. The aqueous sheath liquid surrounds the droplets, and by hydrodynamic focusing maintains the single file order of the droplets. As the droplets travel through the sheath liquid, solvent slowly partitions out of the droplets and into the catch liquid, ultimately causing the precipitation of uniform, monodisperse microspheres of homogeneous composition. During particle formation a stock solution of surfactant (3% (v/v) Tween 20 or PEG) was added to reduce clumping. The microspheres were collected in a 4 L glass beaker and left to cure. This step of the process is needed to remove solvent that remains in the microspheres and it allows the particles to sediment. Following the curing process, the excess catch liquid was decanted and the microspheres were concentrated to a volume of 50 mL. The following settings and specifications were used in this work: tip diameter, 46 µm; frequency, 12.5 kHz; polymer flow rate, 0.5 mL/min; water flow rate, 0.8 mL/min; surfactant flow rate, 1 drop/5–10 sec; curing duration, 2–3 d.

Measurements. Response curves for systems of type 1 were measured in aqueous solutions containing 0.1 M backgrounds of the investigated anions. Sample pH was adjusted with either 1 M HCl or 1 M $HNO_3$ and 1 M NaOH. Solutions ranging from pH 1–4 were unbuffered, while those ranging from pH 5–6 were buffered with 1 mM citric acid, and those ranging from pH 7–9 were buffered with 1 mM boric acid and 1 mM $NaH_2PO_4$. Both type 1 thin films and particles were measured after conditioning for approximately 12 h in 100 mL unstirred samples. For type 1 particle immobilization, cover slips (22 $mm^2$) were placed at the bottom of the sample containers and a 50 µL aliquot of particles was added. After approximately 12 h, the particles had settled and were adsorbed to the slides.

The $K^+$ response curves (type 2) were measured in potassium chloride solutions buffered to pH 7.15 with 2 mM HEPES and 0.6 mM NaOH. Both thin films and particles were conditioned at least 24 h in order for complete equilibration to occur. For immobilization of type 2 particles, 50 µL of particle solution was deposited onto cover slips and the water was allowed to evaporate, leaving adsorbed particles. Prior to measurements slides were stored at least 24 h in the dark in 2 mM HEPES buffer, pH 7.15.

Instrumentation. A Nikon Eclipse E400 microscope equipped with an epifluorescence attachment (Southern Micro Instruments, Marietta, Ga.) and a PARISS® Imaging Spectrometer (Lightform Inc., Belle Mead, N.J.) coupled to a CCD detector were used to optically characterize the sensing films and particles (with 510–560 excitation filter, 565 nm dichroic mirror, and 590 nm long-pass emission filter). (15) Data processing was done on a PC using PARISS® Imaging Software v. 6.0. Ratiometric analysis of fluorescence was done using peak intensities located at 643 and 683 nm for type 2 systems, while for type 1 systems peak intensities at 615 and 683 nm or 643 and 725 nm were used, which correspond to protonated and deprotonated forms of the chromoionophore, respectively. A neutral density filter, 4, was used in conjunction with exposure times of 500 and 100 ms for type 1 and type 2 systems, respectively.

Scanning electron micrographs (SEMs) were obtained using a Zeiss DSM 940 Scanning, Electron Microscope at 5 kV. A drop from a high-density particle solution was evaporated onto an aluminum stub. The sample was sputter-coated for 60 s at 30 µA with 10–20 nm of Au/Pd on a Pelco SC-7 Auto Sputter-Coater (Ted Pella Inc., Redding, Calif.). Particle sizing was done on a 256 channel Coulter Multisizer II in ISOTON II solution with an aperture diameter of 100 µm.

Results and Discussion

Figure 4:
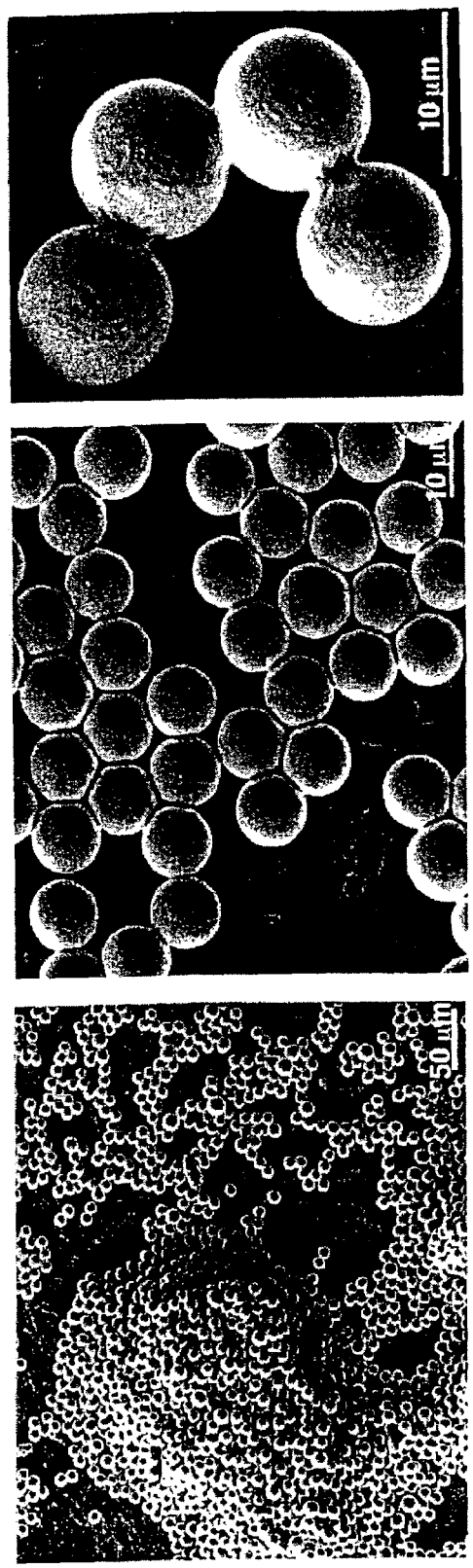
FIG. 4 shows scanning electron micrographs of MMA-DMA microspheres fabricated with a particle casting apparatus.

MMA-DMA microspheres were mass-fabricated using a high-throughput particle casting apparatus that has previously been described(16). As many as 20,000 particles of uniform size and homogeneous composition can be produced each second with this technique. FIG. 4 shows scanning electron micrographs of MMA-DMA microspheres prepared by this method. It is apparent from the figure that the particles are uniform in size and that they possess a spherical shape with no noticeable surface defects. A commercial sizing instrument found the average diameter of the microspheres to be 10.0±0.9 µm (N=5452) over the particle range of 6 to 60 µm (see FIG. 5). For statistical analyses, events below 6 µm were excluded due to the presence of non-spherical debris that is commonly observed.

One advantage that MMA-DMA particles have over PVC-DOS particles, fabricated using the same procedure, is their lack of coalescence during the casting and/or curing processes. The histograms in FIG. 5 show no signs of particle agglomeration for the particles made with MMA-DMA (right), which can be deduced by the absence of doublet and triplet particle distributions often seen in analogous particles made with PVC-DOS (left). This lack of coalescence, in combination with a very narrow size distribution, makes MMA-DMA microspheres suitable for incorporation into several popular sensing platforms, including lab-on-a-chip technologies(57), bundled optical fiber arrays (58), micro-well plate-format assays(59), and flow cytometry(17)(60).

Initial studies aimed at determining the efficacy of MMA-DMA as a suitable plasticizer-free matrix for bulk extraction processes were performed using particles containing only a neutral H+-selective chromoionophore, ETH 5294 (type 1). Optodes of this type function by way of an anion-proton coextraction mechanism(15), whereby the chromoionophore changes its optical properties (i.e., fluorescence) upon the selective extraction of $H^+$. In order to maintain electroneutrality within the sensing matrix, the influx of positive charge must be compensated for by the concerted extraction of a sample anion of equal and opposite charge. The equilibrium describing this process appears as Eqn. 2(15):

$$C(org) + H^+(aq) + A^-(aq) \rightleftharpoons CH^+(org) + A^-(org) \quad (2)$$

where C and CH$^+$ are the deprotonated and protonated forms of the lipophilic chromoionophore ETH 5294, respectively, and H$^+$ and A$^-$ are protons and sample anions, respectively. The notations (org) and (aq) denote organic and aqueous phases, respectively. The expression describing the equilibrium constant, K$_{coex}$, for this process can be found as Eqn. 3(32).

$$K_{coex} = \frac{(1-\alpha)}{\alpha a_{H^+} a_{A^-}} \quad (3)$$

In Eqn. 3, $a_H^+$ and $a_A^-$ are the activities of sample protons and anions in the aqueous phase, respectively, and $\alpha$ and $1-\alpha$ are the degree of chromoionophore deprotonation and protonation, respectively. Eqn. 3 assumes that ion pairing predominates within the organic phase between the protonated chromoionophore and the extracted sample anion. This behavior is quite common in poly(vinyl chloride) sensing membranes plasticized with a polar plasticizers such as DOS(2). Very recently, work done in our group has determined potentiometrically, using solvent polymeric membranes, that the response behavior of MMA-DMA is quite similar to DOS(25). Therefore, it is plausible to assume that ion pairing also predominates within the particles and films fashioned from MMA-DMA.

Figure 6:
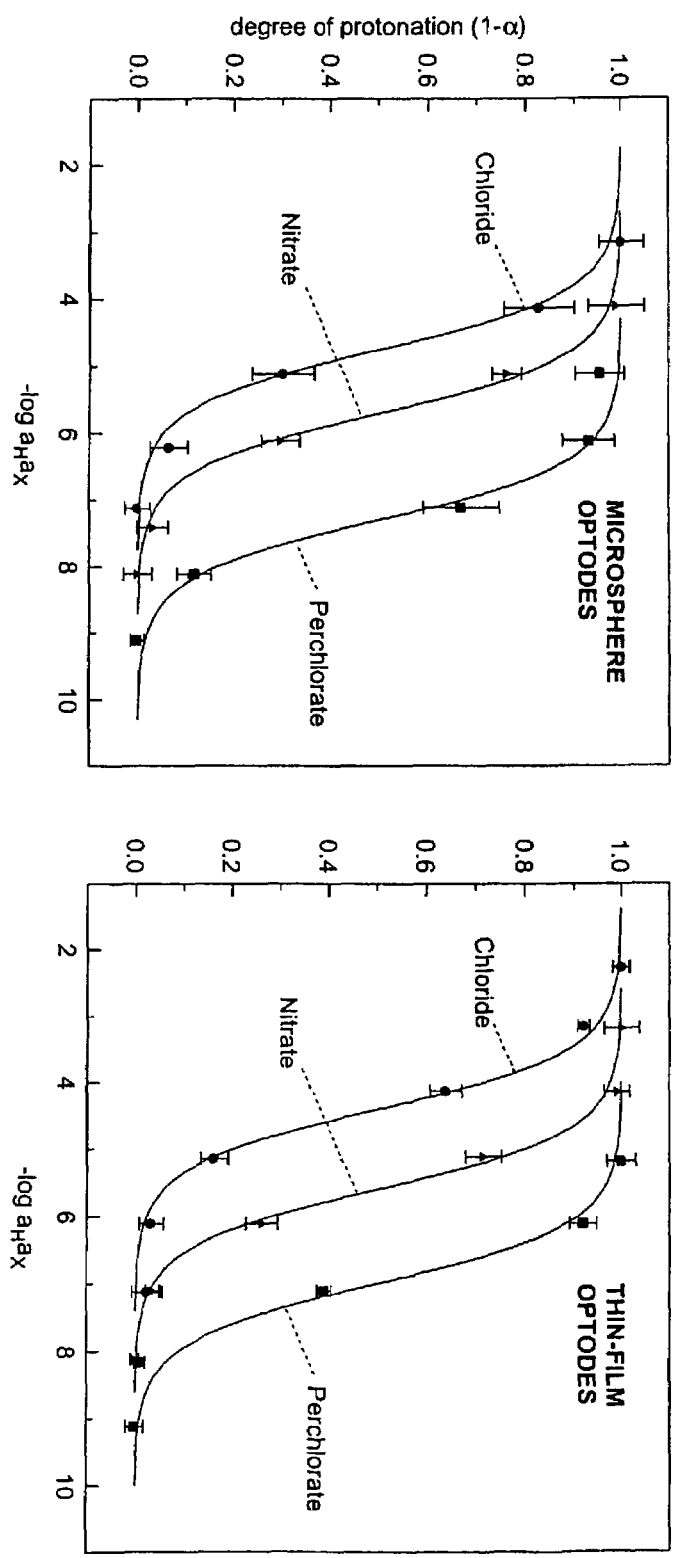
FIG. 6 shows normalized response curves for type 1 particles (left) and thin films (right) to changes in the activity product of anions and hydrogen ions in the sample. Data points are the average of 10 measurements and the solid lines are the theoretically predicted responses (Eqn. 3) towards the sample anions ● chloride, ▲ nitrate, and ■ perchlorate. For particles log $K_{coex}$=4.8 for Cl—, 5.7 for $NO_3$—, and 7.3 for $ClO_4$—. For films log $K_{coex}$=4.4 for Cl—, 5.6 for $NO_3$—, and 7.0 for $ClO_4$—.

The response of type 1 particles towards the sample anions studied, Cl—, NO$_3$—, and ClO$_4$—, is compared to analogous thin films in FIG. 6. Each data point is the average of 10 measurements and the solid lines are the theoretically predicted responses according to Eqn. 3. Response curves were generated using ratiometric fluorescence analysis as previously reported(15)(16). The peak intensities used correspond to the maxima for the protonated and deprotonated forms of ETH 5294. Normalization of the intensity ratios in terms of 1–$\alpha$ was done using the following equation:(11)

$$1 - \alpha = \frac{F_p - F}{F_p - F_d} \quad (4)$$

where 1–$\alpha$ is the degree of protonation of ETH 5294, $F_p$ and $F_d$ are the fluorescence intensity ratios corresponding to the fully protonated and deprotonated forms of ETH 5294, respectively, and F is an observed intensity ratio for a given sample. The coextraction equilibrium constants, K$_{coex}$, were determined by fitting the data points to the theoretically predicted response curves (Eqn. 3). The trend of anion preference observed should obey the well-known Hofmeister selectivity pattern, which is directly related to the hydration enthalpies of the extracted anions. Indeed, this trend was observed both in particulate and thin film-based MMA-DMA optodes, as evidenced in FIG. 6. For particles, log K$_{coex}$=4.8 for Cl—, 5.7 for NO$_3$—, and 7.3 for ClO$_4$—, while for films log K$_{coex}$=4.4 for Cl—, 5.6 for NO$_3$—, and 7.0 for ClO$_4$. Note that both the particles and thin films have very similar K$_{coex}$ values, thus suggesting that the particles function in complete analogy to the thin films.

In order to assess whether MMA-DMA (1) was suitable for truly ion-selective sensing, particles were incorporated with a neutral K+-selective ionophore (BME-44), anionic sites (NaTFPB), and ETH 5294. Optodes of this type function by way of an ion-exchange mechanism. The cation-exchanger facilitates extraction of primary ions into the sensing phase (i.e., particle or film) where they are selectively complexed by the ionophore. The influx of positive charge is compensated for by the concomitant expulsion of protons from the chromoionophore into the sample. It is the change in chromoionophore protonation that provides the analytical signal for quantifying this process. The equilibrium describing the ion-exchange mechanism used here is given below(56)(61).

$$I^+(aq) + L(org) + CH^+(org) + R^-(org) \rightleftharpoons IL^+(org) + C(org) + R^-(org) + H^+(aq) \quad (5)$$

In Eqn. 5, I$^+$ and H$^+$ are primary ions and protons, respectively, L and IL$^+$ are the free and complexed ionophore, respectively, C and CH$^+$ are the deprotonated and protonated forms of the chromoionophore, respectively, and R$^-$ represents anionic sites.

Unfortunately, particles prepared with this polymer took at least 4 days to respond. Therefore, modifications were made to the reaction conditions and MMA-DMA (2) was prepared. The particle response towards K$^+$ and the selectivity observed with this new polymer are compared to analogous thin film optodes in FIG. 7. Each data point is the average of 10 measurements and the solid and dashed lines are the theoretically predicted responses according to the following equation:(56)

$$a_I = \frac{(a_{H^+})^{z_I}}{K_{exch}} \left(\frac{\alpha}{1-\alpha}\right)^{z_I} \frac{(R_T - (1-\alpha)C_T)}{Z_I \left(L_T - \frac{n_I}{Z_I}\{R_T - (1-\alpha)C_T\}\right)} \quad (6)$$

where $a_I$ and $a_H^+$ are the activity of the primary ion and protons, respectively, K$_{exch}$ is the ion-exchange constant for the primary ion, z$_I$ is the charge of the primary ion, $\alpha$ and 1–$\alpha$ are the degree of chromoionophore deprotonation and protonation, respectively, n$_I$ is the binding stoichiometry of the primary ion to the ionophore, and R$_T$, L$_T$, and C$_T$ are the total concentrations of ionic sites, ionophore, and chromoionophore, respectively.

Figure 7:
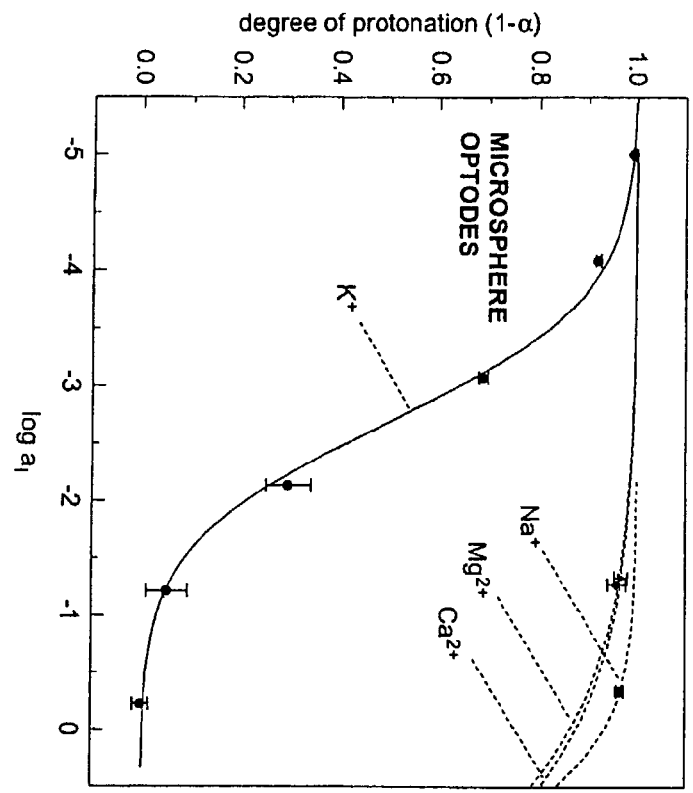
FIG. 7 shows normalized response curves for $K^+$-selective (type 2) particles and analogous thin film optodes towards changes in the potassium activity of the sample. Data points are the average of 10 measurements, and the solid and dashed lines are the theoretically calculated response curves (Eqn. 5) normalized to pH 7.15. The symbols represent ● potassium, ▲ calcium, ♦ magnesium, and ■ sodium. Log $K_{exch}$=−4.7 for particles, and −4.4 for thin film optodes. Log $K_{K^+,Na^+}^{opt}$=−4.0 for particles, and −3.4 for films.
Figure 7:
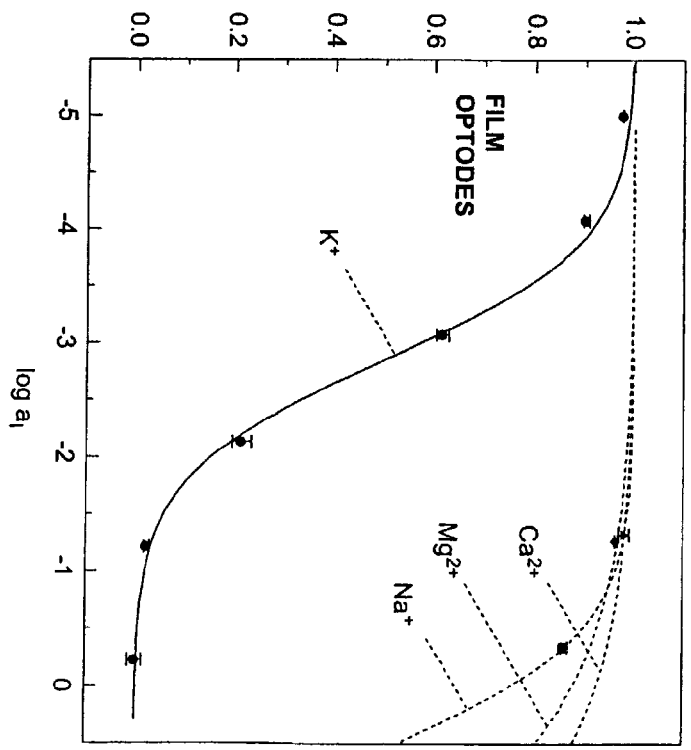

The dynamic range and sensitivity of the particle responses shown in FIG. 7 are in complete agreement with the thin film optode response. It is apparent that the particles function according to classical optode theory and that the observed response behavior can be corroborated with thin films made from MMA-DMA. The selectivity observed for the MMA-DMA particles agrees well with that previously reported for PVC-DOS(15) and DMA-DOS(13) particles (see Table 4). The response time of the particles prepared using MMA-DMA (2) is approximately 12 hours. Although not ideal, improvements are underway in our laboratory addressing this issue. MMA-DMA polymers containing a grafted ionophore have responded as quickly as 15 minutes (data not shown). Therefore, through polymerization modifications and optimization of sensing component concentrations it should be feasible to improve the response time of the MMA-DMA sensing microspheres immensely. Notwithstanding the response time challenge, the MMA-DMA polymer matrix is otherwise fully functional for use in bulk optodes. It is noteworthy to mention that the response time of ISEs fashioned from MMA-DMA has reportedly been quite rapid and in complete agreement with plasticized PVC membranes(25).

Conclusion

Plasticizer-free microspheres incorporated with active sensing components for ionophore-based sensing and extraction have been prepared from a novel methyl methacrylate-decyl methacrylate copolymer and mass-produced using a high-throughput particle casting apparatus. Particles containing chromoionophore only (type 1), responded according to optode theory and demonstrated a Hofmeister selectivity pattern, while type 2 particles, selective for potassium, exhibited a functional response and selectivity comparable to analogous DOS-plasticized particles based on PVC and DMA matrices. In addition, the response behavior observed in both type 1 and type 2 particles was in complete agreement with analogous films. The particles described herein were found to be uniform in shape and size, with a mean particle diameter of ~10 μm. An absence of microsphere agglomeration tendencies is promising for the incorporation of ion-selective microspheres into popular sensing platforms for multianalyte analysis, such as flow cytometry, microfluidic devices, plate-format assays, and bundled optical fiber arrays.

TABLE 4

ION-EXCHANGE CONSTANTS FOR K+-SELECTIVE (TYPE 2) MMA-DMA MICROSPHERES AND A COMPARISON OF OPTICAL SELECTIVITY COEFFICIENTS FOR VARIOUS PARTICLE-BASED SENSING SPHERES.

| | MMA-DMA[a] | | | | PVC-DOS[a] | DMA-DOS[b] |
|---|---|---|---|---|---|---|
| | log $K_{exch}$ | | log $K_{K,J}^{opt}$ | | log $K_{K,J}^{opt}$ | log $K_{K,J}^{opt}$ |
| J+ | Films | Particles | Films | Particles | Particles | Particles |
| Li+ | −4.4 | −4.7 | 0 | 0 | 0 | 0 |
| Na+ | −7.9 | −8.8 | −3.4 | −4.0 | −3.7 | −3.3 |
| Ca2+ | −17.2 | −16.8 | −5.3 | −4.7 | −4.7 | |
| Mg2+ | −16.7 | −16.7 | −4.8 | −4.6 | | |

[a]From [18]
[b]From [16]

EXAMPLE III

Closo-Dodecacarboranes as Ion-Exchangers in Cation-Selective Chemical Sensors Reagents. For membrane preparation, poly(vinyl chloride) (PVC), bis(2-ethylhexyl sebacate) (DOS), 2-nitrophenyl octyl ether (NPOE), sodium tetrakis[3,5-bis(trifluoromethyl)phenyl]borate (NaTFPB), 4-tert-butylcalix[4]arene-tetraacetic acid tetraethyl ester (sodium ionophore X), 2-dodecyl-2-methyl-1,3-propanediyl bis[N-[5'-nitro(benzo-15-crown-5)-4'-yl]carbamate] (potassium ionophore III, BME-44) and tetrahydrofuran (THF) were of Selectophore quality from Fluka (Milwaukee, Wis.). Cesium carborane ($CsCB_{11}H_{12}$) and silver 7, 8, 9, 10, 11, 12-hexabromocarborane ($AgCB_{11}Br_6H_6$) were of the highest quality available from Strem Chemicals (Newburyport, Mass.). Tris(hydroxymethyl)aminomethane (TRIS) was of ACS grade from Aldrich (Milwaukee, Wis.). Chloride salts of lithium, sodium, potassium, calcium, and magnesium were puriss quality from Fluka. All salt solutions were made with deionized Nanopure water (18 MΩ cm).

For syntheses, triflic acid (99%) and bromine (99.8%) were purchased from Alfa Aesar (Ward Hill, Mass.). Trimethylammonium chloride (98%), octadecanoic acid chloride, 4-aminoazobenzene, triethylamine (99.5%), and lithium aluminum hydride were acquired from Aldrich. Diethyl ether, dichloromethane, toluene, and hexane were ACS grade from Fisher Scientific (Norcross, Ga.).

Syntheses. Synthesis of $[Me_3NH][1-H-CB_{11}Br_{11}]$. The synthesis of trimethylammonium-2, 3, 4, 5, 6, 7, 8, 9, 10, 11, 12 undecabromocarborane (TMAUBC) was performed according to the procedure previously reported by Xie et al.,(68) but at half scale. To summarize, a thick-walled Pyrex tube was charged with $CsCB_{11}H_{12}$ (0.05 g, 18 mmol), bromine (0.5 mL, 9.7 mmol), and triflic acid (0.5 mL, 5.65 mmol). The tube was sealed under vacuum and placed in an oven, which was ramped to 200° C. and maintained for 4 days. After removal of excess bromine and triflic acid the brown residue was washed with a 5% (w/v) solution of NaOH until a neutral pH was reached. The solution was extracted with diethyl ether (3×20 mL), and after concentrating, an aqueous solution of $Me_3NHCl$ was added dropwise until no more precipitate formed. The white precipitate was filtered off, washed with deionized water and dried under vacuum, giving $[Me_3NH][1-H-CB_{11}Br_{11}]$ as a white solid (147 mg, 76% yield). The structure of $[Me_3NH][1-H-CB_{11}Br_{11}]$ was confirmed by negative ion FAB-MS, $^1$H-NMR (250 MHz, acetone-$d_6$), and IR. Elemental analysis calculated for $C_4H_{11}NB_{11}Br_{11}$ (1071.00): C, 4.48; H, 1.11; N, 1.31. Found: C, 4.92; H, 1.15; N, 1.33.

The procedure for the synthesis of ETH 5315 has previously been described(72), and gave a yield of 163 mg (20%). The structure was confirmed by $^1$H-NMR (250 MHz, $CDCl_3$) and FAB-MS.

Optode Leaching Experiments. Optode membranes for leaching experiments contained 1.8 mg (16.7 mmol/kg) ETH 5315, 155 mg DOS (66 wt. %), 78 mg PVC (33 wt. %), and either 4.7 mg NaTFPB (22 mmol/kg) or 5.7 mg (22 mmol/kg) $[Me_3NH][1-H-CB_{11}Br_{11}]$. The components were dissolved in 1.5 mL THF. From each cocktail, two membranes of the same composition were cast onto two 35 mm quartz disks by means of a spin-coating device(73). After air-drying the films for one hour they were placed in a flow-through cell(1), which was mounted into a Hewlett-Packard 8452A diode array UV-VIS spectrophotometer and filled with 0.2 M HOAc. The solution was replaced after four hours of stasis by flowing 0.2 M HOAc continuously through the flow cell at a rate of 1.2 mL/min. Absorption spectra were recorded between 300 and 800 nm at one minute intervals.

Optode K+ Response. A cocktail containing 4.72 mg (20 mmol/kg) of the potassium-selective ionophore BME-44 (potassium ionophore III), 1.37 mg (10 mmol/kg) of the chromoionophore ETH 5294 (chromoionophore I), 2.75 mg (10 mmol/kg) of the anionic site TMAUBC, 78.16 mg (33 wt. %) PVC, and 154.78 mg (66 wt. %) DOS was dissolved in 1.5 mL THF. A film was cast onto a quartz disk as mentioned above. Samples made from the chloride salts of potassium, sodium, and calcium were buffered with 1 mM TRIS, pH 7.46. The film was allowed to equilibrate 15 min prior to measuring. A fluorescence microscope was used to assess chromoionophore protonation as previously described(15). Fluorescence was collected using a filter cube with a 510–560 nm excitation filter, a 565 nm dichroic mirror, and a 595 nm long pass emission filter, and spectrally resolved with a dispersing element. Neutral density filters 4 and 8 were used in conjunction with a 40× objective lens. An exposure time of 1000 ms was used for spectral acquisitions.

Membrane Preparation and Potentiometric Measurements. ISE membranes of ca. 200 μm thickness were prepared by pouring a solution of about 140 mg total components, dissolved in 1 mL THF, into 22 mm glass rings affixed onto glass plates. After solvent evaporation, 6 mm diameter membrane disks were cut from the parent membrane and assembled into Philips Electrode bodies. A four electrode batch was fabricated for each composition examined which consisted of 10 mmol/kg ion-exchanger i.e., TMAUBC or NaTFPB (0.9–1.1 wt. %), plasticizer DOS or o-NPOE 66 wt. % and PVC 33 wt %. For comparison of sodium ISE responses incorporating either TMAUBC or NaTFPB as ion-exchanger, the membranes also contained 20 mmol/kg of the sodium ionophore X and plasticizer DOS at the same compositions as stated above. Electrodes containing the TMAUBC ion-exchanger were pre-conditioned in $10^{-2}$ M LiOH for 4 to 6 hours in order to deprotonate and extract trimethylammonium into the aqueous phase. An 8 hour conditioning time in a $10^{-4}$ M $CaCl_2$ solution followed for all electrodes. The internal filling solutions used was $10^{-3}$ M $CaCl_2$ for electrodes containing the ion exchangers only and $10^{-3}$ M NaCl for Na-X based electrodes. Selectivity measurements were all determined from calibration curves obtained in the $10^{-4}$ M to $10^{-1}$ M range of the ions tested in the order of the more to least discriminated ion. Calculations were obtained based on readings taken at the highest concentration level measured. All EMF measurements were made against a Ag/AgCl reference electrode (Metrohm 6.0729.100) with a 1M LiOAc bridge electrolyte. The instrumentation used to acquire potentiometric data has been described earlier(39). Measurement values were corrected for liquid junction potentials using the Henderson formalism and ion activities were calculated according to the Debye-Hückel approximation(74).

Results and Discussion

It has been known for many years that decomposition of tetraphenylborates occurs via hydrolysis in acidic media(61)(63)(64). Experiments comparing the rate of decomposition of various tetraphenylborate derivatives has previously been reported by Simon and coworkers(63). They found that the derivative with the slowest decomposition rate was the highly substituted sodium tetrakis[3,5-bis(trifluoromethyl)phenyl]borate (NaTFPB). The presence of strong electron-withdrawing groups on this compound decreases the tendency for cleavage of the boron-phenyl bond, because the amount of localized charge at the ipso carbons is significantly reduced(64) as compared to the unsubstituted analog. Decomposition experiments comparing the chemical stability of TFPB$^-$ in acid with that of various carborane anions were done using optode films. By using an optode film that contains a lipophilic anion of interest and a chromoionophore with an acidic pKa value (ETH 5315, pKa=5.2(75)), the rate of anion decomposition and/or leaching can be determined. An observed decrease in the absorption peak corresponding to the protonated form of the chromoionophore indicates anion leaching or decomposition. As the anion leaves the film, a hydrogen ion is abstracted from the chromoionophore in order to maintain charge neutrality.

Figure 9:
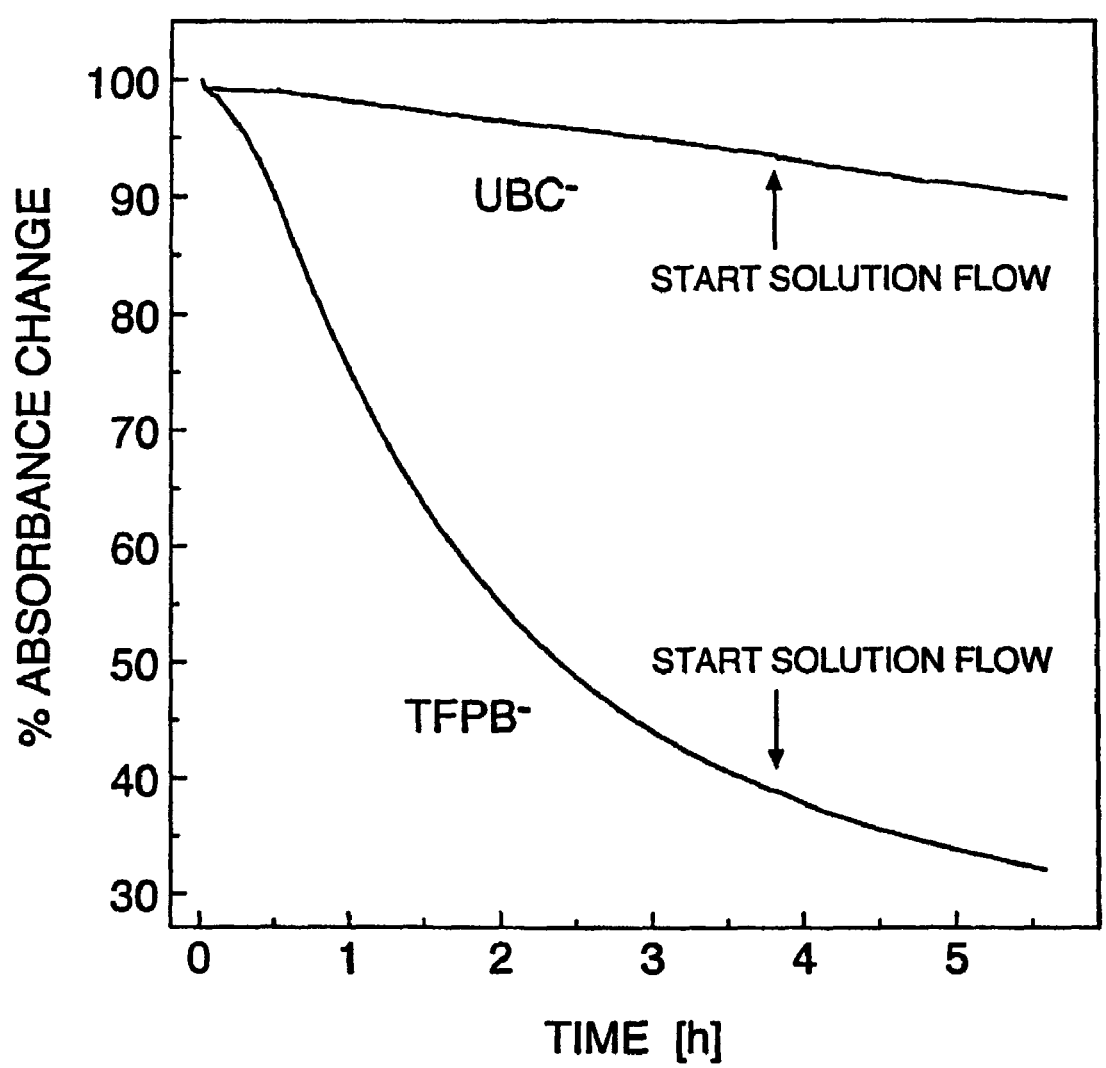
FIG. 9 shows acid decomposition of anionic sites in DOS-PVC (2:1) optode membranes containing ETH 5315, visualized by a decrease in absorbance of the protonated form at 518 nm.

Initial studies evaluated the stability and lipophilicity of the commercially available anions, $CB_{11}H_{12}^-$ and $CB_{11}Br_6H_6^-$. It is expected from the fragment method for the estimation of octanol-water partition coefficients(76) that the substitution of hydrogens by halogens increases the lipophilicity of a compound. Indeed, the unsubstituted carborane anion possessed insufficient lipophilicity and was not able to fully protonate the chromoionophore, although thick ISE membranes for sodium, potassium and lead containing this anion were functional (data not shown). The hexabrominated carborane anion, however, was able to fully protonate the chromoionophore, but after only two hours complete leaching from the optode film was observed (data not shown). This led to the search and synthesis for an even more lipophilic carborane anion, the perbrominated 1-H—$CB_{11}Br_{11}^-$. A comparison of the leaching/decomposition rates of NaTFPB and TMAUBC is shown in FIG. 9. The tetraphenylborate derivative is completely lost in approximately 6 hours, while in the same time period, the perbrominated carborane shows less than a 10% signal decrease. It is clearly demonstrated that I-H—$CB_{11}Br_{11}$ has sufficient lipophilicity and chemical stability, as compared to NaTFPB. The rate of leaching for both anions appears to be slightly increased by changing the flow rate of the contacting acetic acid solution. This is illustrated in FIG. 9 by the small rate increase upon initiation of continuous flow with 0.2 M acetic acid. The rate of decomposition of the NaTFPB reported here differs substantially from that previously reported in the literature(63).

The results shown in FIG. 9 demonstrate that TMAUBC has superior lipophilicity/stability under the conditions shown than the best tetraphenylborate reported to date. Nonetheless, even more lipophilic carborane derivatives are still desired, because TMAUBC exhibited an approximate 10% decrease in absorbance of the protonation peak of ETH 5315, demonstrating that some loss does still occur. Fortunately, because of the versatile functionalization chemistry of carboranes, lipophilicity can easily be tailored by substitution with heavier halogen substituents such as iodine(68)(71), or alkyl groups(69) at the boron vertices. Furthermore, substitution may also occur at the carbon vertex. Many substituted alkyl and phenyl derivatives have been described (70)(71), and exploration of some of these compounds is in progress in our laboratory.

In addition to their use in the leaching studies, optodes were used to evaluate the ion-exchanging capabilities of UBC$^-$ in potassium-selective optical thin films. The normalized response curve of UBC$^-$ containing films for potassium appears as FIG. 10 and is compared to the analogous behavior of TFPB$^-$ containing optode films. The potassium activity in a given sample was determined by using the fluorescence emission of the neutral chromoionophore, ETH 5294. Peaks at 655 and 693 nm, corresponding to the deprotonated and protonated form of the chromoionophore, respectively, were used to monitor ion-exchange. As potassium ions enter the film, the chromoionophore is deprotonated to maintain electroneutrality, this corresponds to a decrease in fluorescence intensity at 693 nm, and conversely, an increase in the deprotonated emission peak at 655 nm. By taking the ratio of these two emission peaks, a response curve may be generated. The use of ratiometric fluorescence measurements to normalize response curves in terms of the degree of protonation of the chromoionophore has been described previously(15). The theoretical response curve used to fit the data in FIG. 10 has been reported repeatedly (72, 77).

Figure 10:
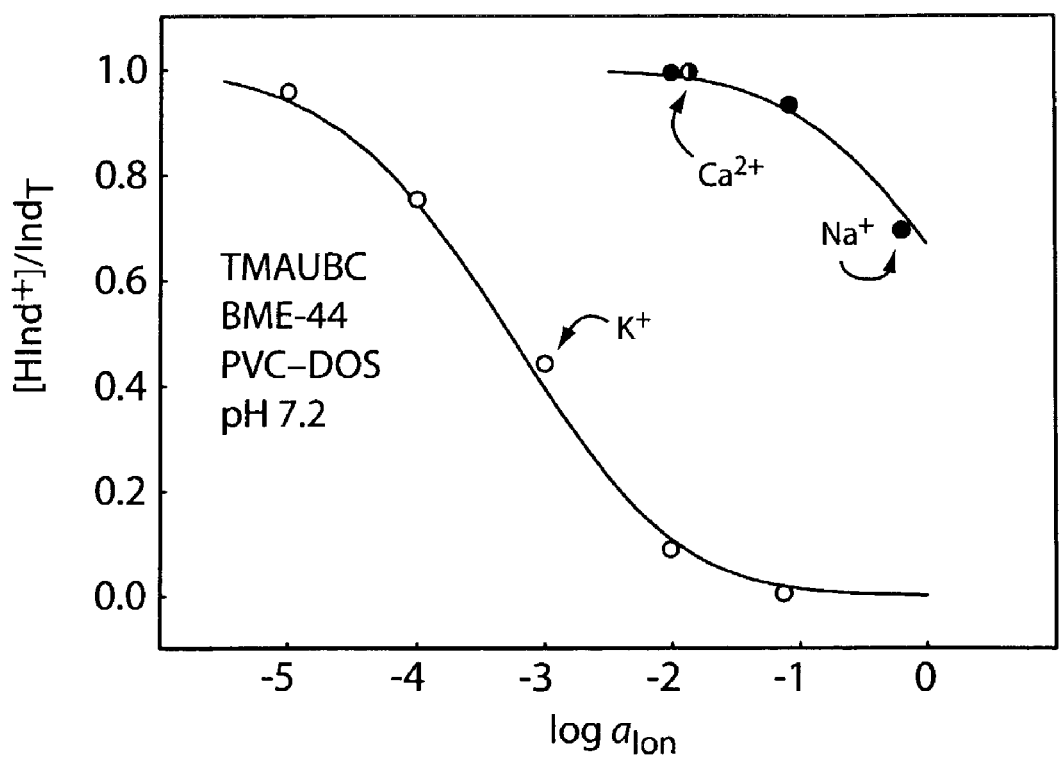
FIG. 10 shows the normalized optical K+ response curves and selectivities over sodium and calcium for thin DOS-PVC (2:1) films containing the potassium ionophore BME-44, the H+-chromoionophore ETH 5294, and either TMAUBC (top) or NaTFPB (bottom) as lipophilic cation-exchangers. The y-axis denotes the mole fraction of protonated chromoionophore (Ind).
Figure 10:
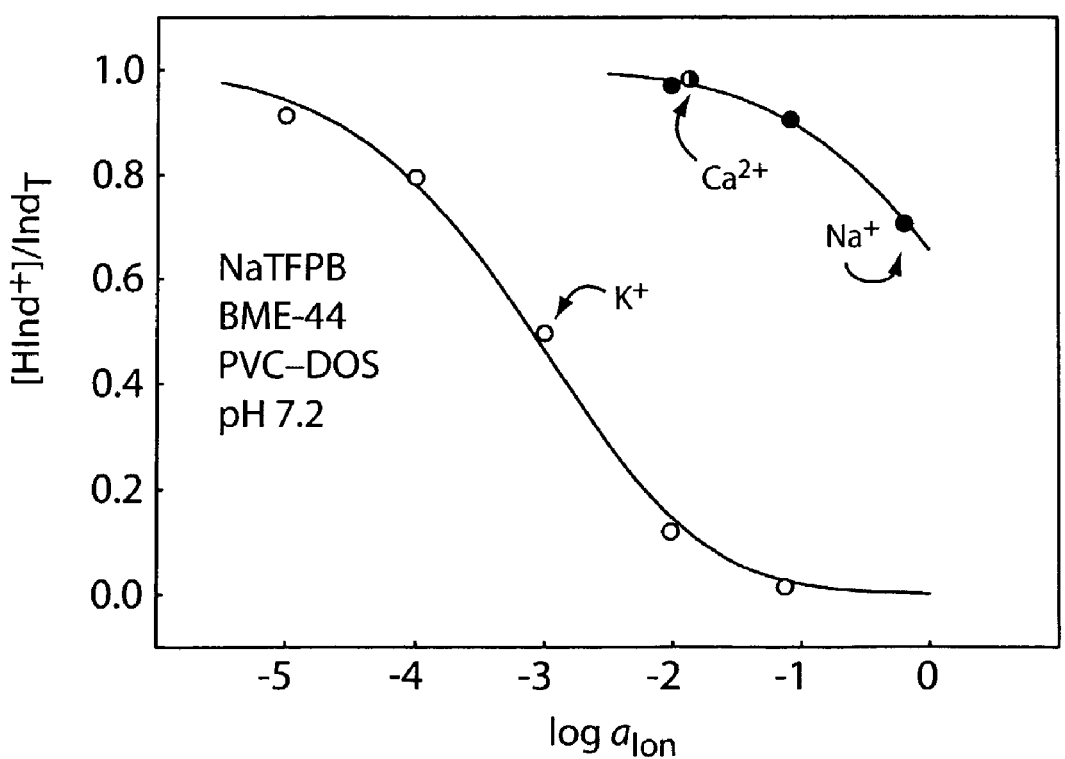

The location of the response curve and the 3 orders of magnitude measuring range shown in FIG. 10 is identical with that found in the literature for the analogous system containing TFPB$^-$ as ionic site(15). In contrast, however, there is a marked improvement in the selectivity of potassium over sodium and calcium in the case of UBC$^-$. Potassium appears to be preferred over calcium by at least 2 orders of magnitude compared to optode data containing TFPB$^-$ as ion-exchanger(15). This might be explained by the ability of carborane anions to form weaker ion pairs than tetraphenylborates(64)(67), which could suppress the extraction of interferents that form weak complexes with the ionophore.

Figure 11:
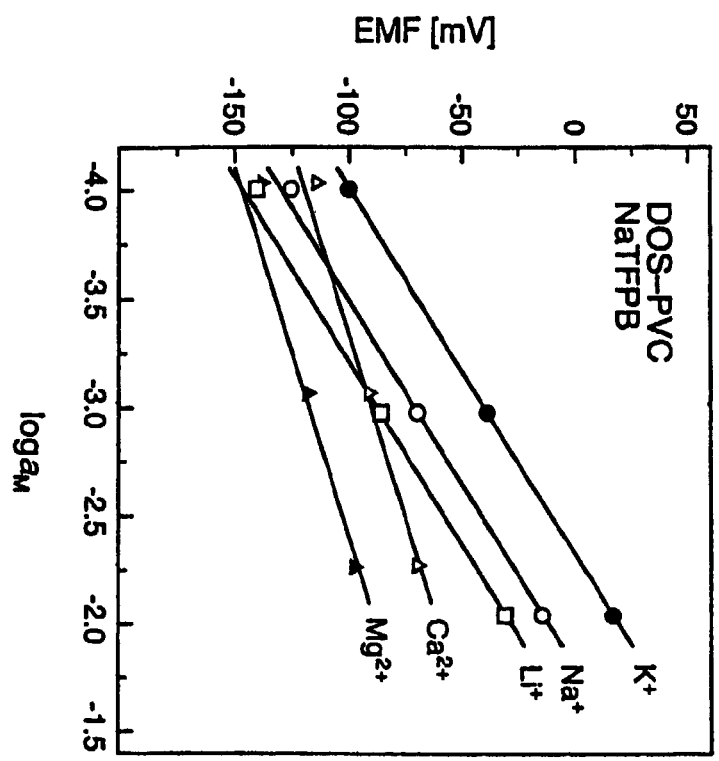
FIG. 11 shows potentiometric selectivity comparison of ionophore-free DOS-PVC (2:1) membranes containing 10 mmol $kg^{-1}$ of either TMAUBC (right) or NaTFPB (left). Solid lines with theoretical slope.
Figure 11:
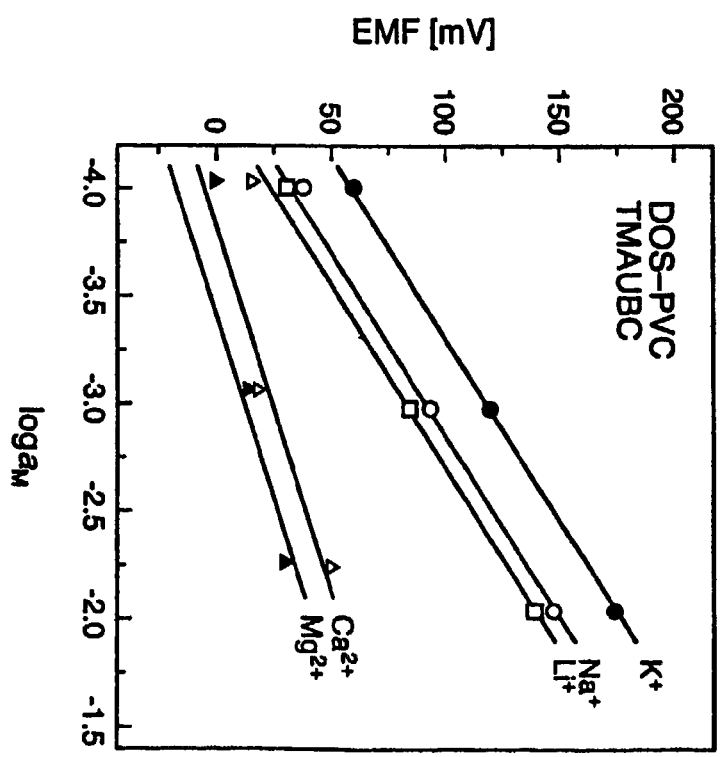

In addition to optical experiments, the selectivity behavior of the perbrominated carborane was evaluated potentiometrically using ionophore-free ISE membranes. As expected, all membranes show a selectivity pattern in order of increasing cation lipophilicity. However, in PVC-DOS membranes containing only UBC$^-$, there was a clear improvement in selectivity over calcium and magnesium of about half an order of magnitude compared to PVC-DOS membranes containing only NaTFPB (See Table 5 and FIG. 11). The electrode slopes were close to Nernstian (see Table 5). This independent experiment is consistent with the selectivity data obtained with the optode films and suggests that TFPB$^-$ forms stronger ion pairs with alkaline earth metals than the lipophilic carborane.

functionalization chemistry make dodecacarboranes a promising alternative to even the best substituted tetraphenylborates known, such as TFPB$^-$. In addition, lack of absorption of the ultraviolet and visible wavelengths make carboranes attractive for optical sensing applications. Surprisingly, a comparison of ion-exchanger ISE membranes containing 1-H—CB$_{11}$Br$_{11}^-$ or NaTFPB demonstrated that ISE membranes containing the carborane showed improved selectivity over calcium and magnesium ions. Furthermore, comparable selectivity was achieved by the perbrominated carborane in membranes containing a sodium-selective ionophore. Bulk optode films containing the potassium-selective ionophore, BME-44, demonstrated that 1-H—CB$_{11}$Br$_{11}^-$ functions as a suitable ion-exchanger, and it

TABLE 5

POTENTIOMETRIC SELECTIVITY COEFFICIENTS AND ELECTRODE SLOPES
FOR ION-SELECTIVE MEMBRANES CONTAINING THE ION-EXCHANGERS TFPB$^-$AND UBC$^-$.

| | log K$_{NaJ}^{pot\,a}$ and electrode slopes$^{a,b}$ for DOS-PVC (2:1) | | | | log K$_{NaJ}^{pot\,b}$ and electrode slopes$^{a,b}$ for NPOE-PVC (2:1) | | | |
|---|---|---|---|---|---|---|---|---|
| Ion J$^{z+}$ | TFPB$^-$ | | UBC$^-$ | | TFPB$^-$ | | UBC$^-$ | |
| Li$^+$ | −0.27 ± 0.02 | 58.4 ± 0.5 | −0.14 ± 0.01 | 57.6 ± 0.2 | −0.6 ± 0.1 | 47 ± 2 | −0.61 ± 0.08 | 31 ± 2 |
| Na$^+$ | 0 | 58.9 ± 0.7 | 0 | 56.5 ± 0.1 | 0 | 51.2 ± 0.7 | 0 | 57.6 ± 0.3 |
| K$^+$ | 0.55 ± 0.02 | 59.1 ± 0.6 | −0.45 ± 0.01 | 56.6 ± 0.3 | −1.3 ± 0.2 | 57.5 ± 0.2 | 1.21 ± 0.01 | 49 ± 2 |
| Mg$^{2+}$ | −2.37 ± 0.08 | 24 ± 3 | −2.91 ± 0.03 | 22.7 ± 0.7 | −1.50 ± 0.06 | 28.1 ± 0.7 | −1.7 ± 0.1 | 14 ± 1 |
| Ca$^{2+}$ | −2.0 ± 0.1 | 28 ± 1 | −2.57 ± 0.04 | 29 ± 2 | −0.99 ± 0.09 | 29 ± 2 | −1.6 ± 0.1 | 20 ± 2 |

$^a$Average from three electrodes; standard deviation given.
$^b$Slope (second column for each data set): between log a = −3.1 and −1.

Figure 12:
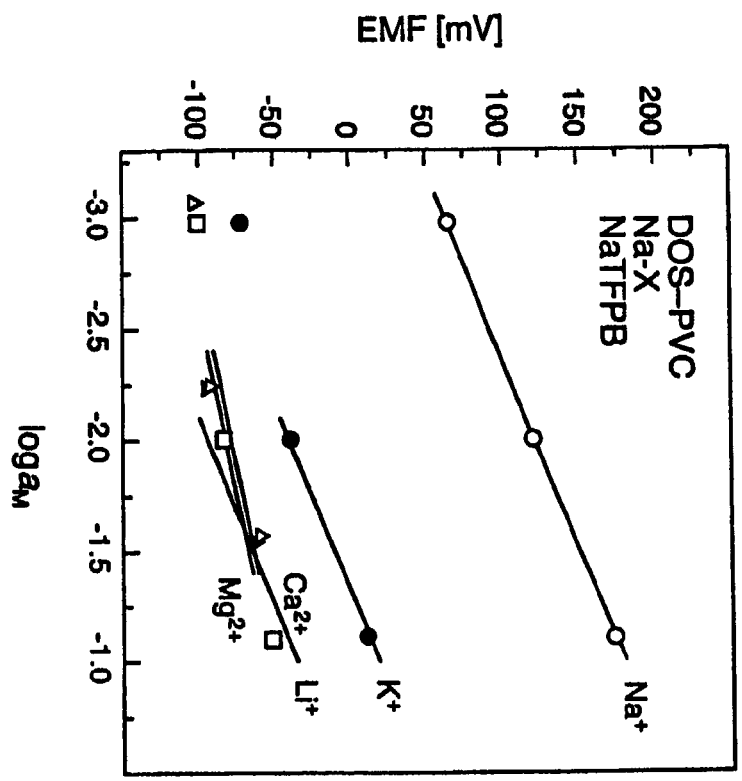
FIG. 12 shows potentiometric selectivity comparison of DOS-PVC (2:1) membranes containing sodium ionophore X, and either TMAUBC or NaTFPB as ionic additives. Solid lines with theoretical slope.
Figure 12:
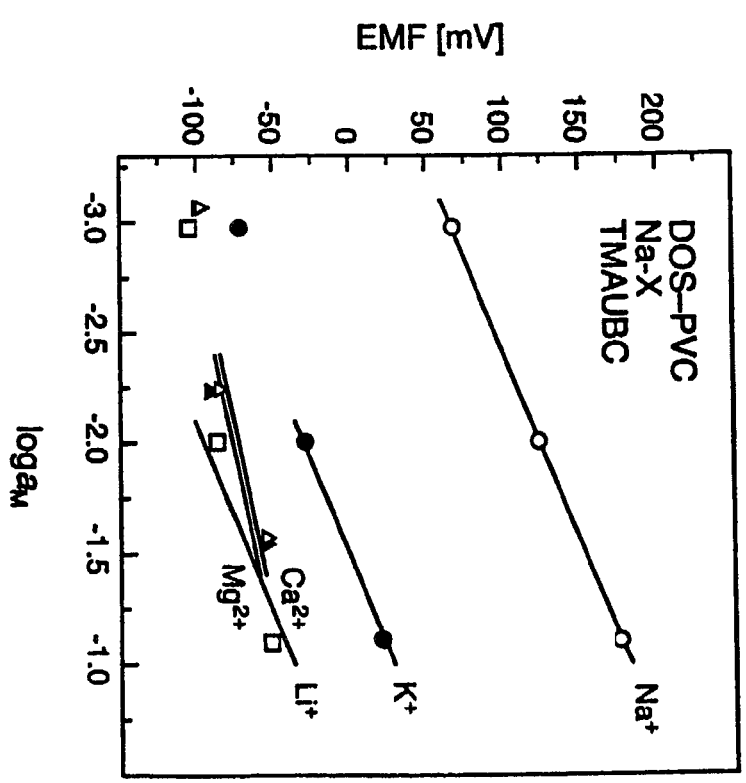

In addition to the selectivity evaluation of 1-H—CB$_{11}$Br$_{11}^-$ in simple ion-exchanger membranes, selectivity was also examined in membranes containing a sodium ionophore. FIG. 12 compares the potentiometric responses of PVC-DOS membranes with sodium ionophore X and either UBC$^-$ or TFPB$^-$ as ion-exchanger. As shown in Table 6, both electrodes exhibit near-Nernstian slopes for Na$^+$ and have nearly identical selectivity coefficients for the discriminating ions tested. Electrode slopes for a number of interfering ions are sub-Nernstian, which indicates that the values found here are conservative upper limits for those ions(39).

TABLE 6

POTENTIOMETRIC SELECTIVITY COEFFICIENTS AND
ELECTRODE SLOPES FOR DOS-PVC (2:1) ION-SELECTIVE
MEMBRANES CONTAINING THE SODIUM IONOPHORE NA-X
AND THE ION-EXCHANGERS TFPB$^-$ and UBC

| | Log K$_{NaJ}^{pot\,a}$ and electrode slopes$^{a,b}$ | | | |
|---|---|---|---|---|
| Ion J$^{z+}$ | TFPB$^-$ | | UBC$^-$ | |
| Li$^+$ | −3.85 ± 0.05 | 25 ± 1 | −3.8 ± 0.2 | 30 ± 2 |
| Na$^+$ | 0 | 57.8 ± 0.2 | 0 | 56 ± 3 |
| K$^+$ | −2.80 ± 0.01 | 43 ± 2 | −2.6 ± 0.2 | 48.9 ± 0.3 |
| Mg$^{2+}$ | −4.32 ± 0.05 | 24.9 ± 0.4 | −4.3 ± 0.2 | 31 ± 5 |
| Ca$^{2+}$ | −4.25 ± 0.03 | 30 ± 2 | −4.1 ± 0.2 | 33 ± 9 |

$^a$Average from three electrodes; standard deviation given.
$^b$Slope (second column for each data set): between log a = −3.1 and −1.

Conclusions

The perbrominated closo-dodecacarborane anion, 1-H—CB$_{11}$Br$_{11}^-$, has been evaluated as an improved ion-exchanger in ion-selective chemical sensors. Superior chemical stability, high lipophilicity and versatile again improves selectivity over sodium and calcium. These results are quite exciting, as they indicate that many important sensing characteristics such as lifetime, signal stability and selectivity can all be significantly improved by introducing this new class of anionic additives. The synthesis of more electron-withdrawing dodecacarborane derivatives with even higher lipophilicity, along with a more detailed characterization of the ion pairing and lipophilicity characteristics is also expected.

The foregoing is meant to illustrate, but not to limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes, which come within the meaning and range of the equivalence of the claims, are to be embraced within their scope.

REFERENCES (1) Morf, W. E.; Seiler, K.; Sorensen, P. R.; Simon, W., *Proceedings of the Fifth Symposium on Ion-Selective Electrodes,* Matrafured, Hungary 1988; Akademiai Kiado; 141–152.

(2) Eugster, R.; Rosatzin, T.; Rusterholz, B.; Aebersold, B.; Pedrazza, U.; Rüegg, D.; Schmid, A.; Spichiger, U. E.; Simon, W. *Anal. Chim. Acta* 1994, 289, 1–13.

(3) Moody, G. J. In *Biosensors & Chemical Sensors;* Edelman, P. G., Wang, J., Eds.; American Chemical Society: Washington, D.C., 1992; Vol. ACS Symposium Series 487, pp 99–110.
(4) Lindner, E.; Cosofret, V. V.; Ufer, S.; Johnson, T. A.; Ash, R. B.; Nagle, H. T.; Neuman, M. R.; Buck, R. P. *Fres. J. Anal. Chem.* 1993, 346, 584–588.
(5) Hileman, B. *C & E News* 2002, 80, 7.
(6) Oesch, U.; Simon, W. *Anal. Chem.* 1980, 52, 692–700.
(7) Dinten, O.; Spichiger, U. E.; Chaniotakis, N.; Gehrig, P.; Rusterholz, B.; Morf, W. E.; Simon, W. *Anal. Chem.* 1991, 63, 596–603.
(8) Reinhoudt, D. N.; Engbersen, J. F. J.; Brzozka, Z. *Anal. Chem.* 1994, 66, 3618–3623.
(9) Song, A.; Parus, S.; Kopelman, R. *Anal. Chem.* 1997, 69, 863–867.
(10) Barker, S. L. R.; Thorsrud, B. A.; Kopelman, R. *Anal. Chem.* 1998, 70, 100–104.
(11) Shortreed, M.; Bakker, E.; Kopelman, R. *Anal. Chem.* 1996, 68, 2656–2662.
(12) Shortreed, M. R.; Dourado, S.; Kopelman, R. *Sens. Actuat. B* 1997, 38–39, 8–12.
(13) Brasuel, M.; Kopelman, R.; Miller, T. J.; Tjalkens, R.; Philbert, M. A. *Anal. Chem.* 2001, 73, 2221–2228.
(14) Peper, S.; Tsagkatakis, I.; Bakker, E. *Anal. Chim. Acta* 2001, 442, 25–33.
(15) Tsagkatakis, I.; Peper, S.; Bakker, E. *Anal. Chem.* 2001, 73, 315–320.
(16) Tsagkatakis, I.; Peper, S.; Retter, R.; Bell, M.; Bakker, E. *Anal. Chem.* 2001, 73, 6083–6087.
(17) Retter, R.; Peper, S.; Bell, M.; Tsagkatakis, I.; Bakker, E. *Anal. Chem.,* 2002, 74, 5420–5425.
(18) Clark, H. A.; Kopelman, R.; Tjalkens, R.; Philbert, M. A. *Anal. Chem.* 1999, 71, 4837–4843.
(19) Yun, S. Y.; Hong, Y. K.; Oh, B. K.; Cha, G. S.; Nam, H.; Lee, S. B.; Jin. J.-I. *Anal. Chem.* 1997, 69, 868–873.
(20) Högg, G.; Lutze, O.; Cammann, K. *Anal. Chim. Acta* 1996, 335, 103–109.
(21) Lindner, E.; Niegreisz, Z.; Toth, K.; Pungor, E.; Berube, T. R.; Buck, R. P. *J. Electroanal. Chem.* 1989, 259, 67–80.
(22) Yoon, I. J.; Lee, D. K.; Nam, H.; Cha, G. S.; Strong, T. D.; Brown, R. B. *J. Electroanal. Chem.* 1999, 464, 135–142.
(23) Bobacka, J.; Ivaska, A.; Lewenstam, A. *Anal. Chim. Acta* 1999, 385, 195–202.
(24) Dimitrakopoulos, T.; Farrell, J. R.; Iles, P. J. *Electroanalysis* 1996, 8, 391–395.
(25) Qin, Y.; Peper, S.; Bakker, E. *Electroanalysis* 2002.
(26) Heng, L. Y.; Hall, E. A. H. *Anal. Chem.* 2000, 72, 42–51.
(27) Heng, L. Y.; Hall, E. A. H. *Electroanalysis* 2000, 12, 187–193.
(28) Malinowska, E.; Gawart, L.; Parzuchowski, P.; Rokicki, G.; Brzozka, Z. *Anal. Chim. Acta* 2000, 421, 93–101.
(29) M. B. Horn, *Acrylic Resins,* Reinhold Publishing Corp., New York 1960.
(30) H. R. Allcock, F. W. Lampe, *Contemporary Polymer Chemistry,* Prentice-Hall Inc., Englewood Cliffs, N.J. 1990.
(31) S. R. Sandler, W. Karo, *Polymer Synthesis,* Academic Press, San Diego, Calif. 1992.
(32) L. Y. Heng, E. A. H. Hall, *Anal. Chim. Acta* 2000, 403, 77.
(33) G. J. Moody, B. Saad, J. D. R. Thomas, *Analyst* 1987, 112, 1143.
(34) T. M. Ambrose, M. E. Meyerhoff, *Anal. Chem.* 1997, 69, 4092.
(35) T. M. Ambrose, M. E. Meyerhoff, *Anal. Chim. Acta* 1999, 378, 119.
(36) T. M. Ambrose, M. E. Meyerhoff, *Electroanalysis* 1996, 8, 1095.
(37) E. Bakker, P. Buhlmann, E. Pretsch, *Chem. Rev.* 1997, 97, 3083.
(38) E. Bakker, *Anal. Chem.* 1997, 69, 1061.
(39) E. Bakker, *J. Electrochem. Soc* 1996, 143, L83.
(40) H. Tamura, K. Kimura, T. Shono, *Bull. Chern. Soc. Jpn.* 1980, 53, 547.
(41) E. Bakker, R. K. Meruva, E. Pretsch, M. E. Meyerhoff, *Anal. Chem.* 1994, 66, 3021.
(42) E. Bakker, A. Xu, E. Pretsch, *Anal. Chim. Acta.* 1994, 295, 253.
(43) C. C. Ku, R. Liepins, *Electrical Properties of Polymers,* New York 1987.
(44) W. E. Morl, *The Principles of Ion-Selective Electrodes and of Membrane Transport,* Elsevier, 1981.
(45) R. Eugster, T. Rosatzin, B. Rusterholz, B. Aebersold, U. Pedrazza, D. Ruegg, A. Schmid, U. E. Spichiger, W. Simon, *Anal. Chim. Acta* 1994, 289, 1.
(46) J. Tarcali, G. Nagy, K. Toth, E. Pungor, *Anal. Chim. Acta.* 1985, 178, 231.
(47) K. Kimura, H. Oishi, T. Miura, T. Shono, *Anal. Chem.* 1987, 59, 2331.
(48) D. Erne, D. Diamond, A. F. Zhukov, F. Brhm, E. Pretsch, W. Simon, *Helv. Chim. Acta.* 1982, 65, 538.
(49) A. Ceresa, E. Pretsch, *Anal. Chim. Acta.* 1999, 395, 41.
(50) M. Telting-Diaz, E. Bakker, *Anal. Chem.* 2002, 73, 5582–5589.
(51) R. Grady, A. Cadogan, T. McKittrick, S. J. Harris, D. Diamond, M. A. McKervey, *Anal. Chim. Acta.* 1996, 336, 1.
(52) E. Lindner, K. Toth, J. Jeney, M. Horvath, E. Pungor, I. Bitter, B. Agai, L. Toke, *Mikrochim. Acta.* 1990, 1, 157.
(53) M. E. Poplawski, R. B. Brown, K. L. Rho, S. Y. Yun, H. J. Lee, G. S. Cha, K-J. Paeng, *Anal. Chim. Acta* 1997, 355, 249.
(54) Mohr, G. J.; Tirelli, N.; Spichiger-Keller, U. E. *Anal. Chem.* 1999, 71, 1534–1539.
(55) Horn, M. B. *Acrylic Resins;* Reinhold Publishing Corp., New York, 1960.
(56) Seiler, K.; Simon, W. *Anal. Chim. Acta* 1992, 266, 73–87.
(57) Goodey, A.; Lavigne, J. J.; Savoy, S. M.; Rodriguez, M. D.; Curey, T.; Tsao, A.; Simmons, G.; Wright, J.; Yoo, S.-J.; Sohn, Y.; Anslyn, E. V.; Shear, J. B.; Neikirk, D. P.; McDevitt, J. T. *J. Am. Chem. Soc.* 2001, 123, 2559–2570.
(58) Ferguson, J. A.; Steemers, F. J.; Walt, D. R. *Anal. Chem.* 2000, 72, 5618–5624.
(59) Swartzman, E. E.; Miraglia, S. J.; Mellentin-Michelotti, J.; Evangelista, L.; Yuan, P.-M. *Anal. Biochem.* 1999, 271, 143–151.
(60) Vignali, D. A. A. *J. Immunol. Meth.* 2000, 243, 243–255.
(61) Bakker, E.; Buhlmann, P.; Pretsch, E. *Chem. Rev.* 1997, 97, 3083–3132.
(62) Bakker, E.; Pretsch, E. *Anal. Chim. Acta* 1995, 309, 7.
(63) Rosatzin, T.; Bakker, E.; Suzuki, K.; Simon, W. *Anal. Chim. Acta* 1993, 280, 197.
(64) Strauss, S. *Chem. Rev.* 1993, 93, 927.
(65) Nishida, H.; Takada, N.; Yoshimura, M.; Sonoda, T.; Kobayashi, H. *Bull. Chem. Soc. Jpn.* 1984, 75, 2600.
(66) Ceresa, A.; Bakker, E.; Hattendorf, B.; Günther, D.; Pretsch, E. *Anal. Chem.* 2001, 72, 343.

(67) Reed, C. *Acc. Chem. Res.* 1998, 31, 133.
(68) Xie, Z.; Tsang, C.-W.; Sze, E. T.-P.; Yang, Q.; Chan, D. T. W.; Mak, T. C. W. *Inorg. Chem.* 1998, 37, 6444.
(69) Tsang, C.-W.; Xie, Z. *Chem. Comm.* 2000, 1839.
(70) Jelinek, T.; Baldwin, P.; Scheidt, W. R.; Reed, C. A. *Inorg. Chem.* 1993, 32, 1982.
(71) Xie, Z.; Tsang, C.-W.; Xue, F.; Mak, T. C. W. *J. Organometallic Chem.* 1999, 577, 197.
(72) Lerchi, M.; Bakker, E.; Rusterholz, B.; Simon, W. *Anal. Chem.* 1992, 64, 1534.
(73) Seiler, K.; Simon, W. *Anal. Chim. Acta* 1992, 266, 73.
(74) Meier, P. C. *Anal. Chim. Acta* 1982, 136, 363.
(75) Bakker, E.; Lerchi, M.; Rosatzin, T.; Rusterholz, B.; Simon, W. *Anal. Chim. Acta* 1993, 278, 211.
(76) Hansch, C.; Leo, A. *Substituent Constants for Correlation Analysis in Chemistry and Biology;* John Wiley & Sons: New York, 1979.
(77) Kurihara, K.; Ohtsu, M.; Yoshida, T.; Abe, T.; Hisamoto, H.; Suzuki, K. *Anal. Chem.* 1999, 71, 3558.
(78) L. Y. Heng, E. A. H. Hall, *Anal. Chem. Acta* 2001, 443, 25

What is claimed is:

1. An ion detective sensor for detecting a target ion in a sample, comprising:
    (a) a self-plasticizing copolymer matrix of methacrylate monomers with $R_1$ and $R_2$ pendant alkyl groups, and
    (b) an ionophore for detecting the target ion, wherein the ionophore is in the self-plasticizing copolymer matrix; wherein $R_1$ is any of $C_{1-3}$ alkyl groups, $R_2$ is any of $C_{4-12}$ alkyl groups, and
wherein the self-plasticizing copolymer has a glass transitional temperature ($T_g$) of about or below 0° C.

2. The ion detective sensor of claim 1, wherein $R_1$ is any of $C_{1-2}$ alkyl groups, and $R_2$ is any of $C_{8-12}$ alkyl groups.

3. The ion detective sensor of claim 2, wherein $R_1$ is a $C_1$ alkyl group, and $R_2$ is a $C_{10}$ alkyl group.

4. The ion detective sensor of claim 1, wherein the self-plasticizing copolymer has a $T_g$ in the range of from about 0° to −90° C.

5. The ion detective sensor of claim 1, wherein the self-plasticizing copolymer has a $T_g$ in the range of from about −5° to −8° C.

6. The ion detective sensor of claim 1, wherein the matrix is in a form of membrane.

7. The ion detective sensor of claim 6, wherein the self-plasticizing copolymer matrix and ionophore are in the form of a membrane for a carrier-based ion-selective electrode.

8. The ion detective sensor of claim 6, wherein the self-plasticizing copolymer matrix and ionophore are in the form of a membrane for a thin film ion-specific optode.

9. The ion detective sensor of claim 1, wherein the matrix is in a form of particles.

10. The ion detective sensor of claim 9, wherein the self-plasticizing copolymer matrix and ionophore are in the form of particles for a particle-based optode.

11. The ion detective sensor of claim 10, wherein the optode has a particle size of from about 3 to 60 µm.

12. The ion detective sensor of claim 1, wherein the ionophore is a target ionophore selective for a target ion selected from a group consisting of $H^+$, $Li^+$, $Na^+$, $K^+$, $Ca^{2+}$, and $Mg^{2+}$.

13. The ion detective sensor of claim 1 further comprising an indicator ionophore.

14. The ion detective sensor of claim 13, wherein the indicator ionophore is selected from a group consisting of a pH indicating chromoionophore, a chromoionophore, a fluoroionophore, a pH indicator, and a pH indicating fluoroionophore.

15. The ion detective sensor of claim 1 further comprising an ion exchanger.

16. The ion detective sensor of claim 15, wherein the ion exchanger is halogenated carborane anion.

17. The ion detective sensor of claim 16, wherein the ion exchanger is trimethylammonium salt of the 2, 3, 4, 5, 6, 7, 8, 9, 10, 11, 12 undecabromocarborane anion, 1-$HCB_{11}Br_{11}$- (TMAUBC).

18. The ion detective sensor of claim 1, comprising a sample, wherein the sample is a body fluid selected from the group consisting of whole blood, spinal fluid, blood serum, urine, saliva, semen, and tears.

19. An ion detective sensor comprising a polymeric matrix of methacrylate monomers with dependent alkyl groups, an ionophore for detecting a target ion, and an ion exchanger TMAUBC, wherein the ionophore and ion exchanger are in the polymeric matrix, and wherein the polymeric matrix has a glass transitional temperature ($T_g$) of about or below 0° C.

20. The ion detective sensor of claim 19, wherein the polymeric matrix and ionophore are in the form of a membrane for a polymeric membrane electrode.

21. The ion detective sensor of claim 19, wherein the polymeric matrix and ionophore are in the form of a membrane for a tbin film bulk optode.

22. The ion detective sensor of claim 19, wherein the polymeric matrix and ionophore are in the form of particles for a particle-based optode.

23. The ion detective sensor of claim 22, wherein the optode has a particle size of from about 3 to 60 µm.

24. The ion detective sensor of claim 19, wherein the ionophore is selective for K+, further comprising a chromoionophore as an indicator ionophore.

* * * * *